United States Patent [19]

Beauchemin et al.

[11] Patent Number: 5,720,971
[45] Date of Patent: Feb. 24, 1998

[54] ENZYME ADDITIVES FOR RUMINANT FEEDS

[75] Inventors: Karen A. Beauchemin; Lyle Rode, both of Lethbridge, Canada; Vincent J. Sewalt, Ardmore, Okla.

[73] Assignee: Her Majesty the Queen in right of Canada, as represented by the Department of Agriculture and Agri-Food Canada, Lacombe, Canada

[21] Appl. No.: 497,913

[22] Filed: Jul. 5, 1995

[51] Int. Cl.$^6$ ...................................................... A23K 1/18
[52] U.S. Cl. ..................... 424/438; 424/442; 424/94.2; 424/94.61
[58] Field of Search ................... 424/438, 942, 424/94.1, 94.2, 94.3, 94.6–94.62; 426/53, 54

[56] References Cited

U.S. PATENT DOCUMENTS

| | | | |
|---|---|---|---|
| 3,492,398 | 1/1970 | Marco et al. | 514/450 |
| 5,314,692 | 5/1994 | Haarasilta et al. | 424/94.2 |
| 5,531,994 | 7/1996 | Schmidt et al. | 424/405 |

FOREIGN PATENT DOCUMENTS

| | | |
|---|---|---|
| 1322159 | 9/1993 | Canada. |
| 88 105409 | 10/1988 | European Pat. Off.. |
| 296 406 A5 | 12/1991 | Germany. |
| 60-75238 | 4/1985 | Japan. |
| 869615 | 5/1961 | United Kingdom. |
| 296 407 A5 | 12/1991 | United Kingdom. |
| 2261877 | 2/1993 | United Kingdom. |
| WO 91/04673 | 4/1991 | WIPO. |
| WO 91/15966 | 10/1991 | WIPO. |
| 92/01389 | 2/1992 | WIPO. |
| 92/10945 | 7/1992 | WIPO. |

OTHER PUBLICATIONS

Bailey, M.J. et al., 1989. "Production of Xylanolytic Enzymes by Strains of Aspergillus". Appl. Microbial. Biotechnol., 1989, 30:5–10.

National Research Council, 1984. "Nutrient Requirements of Beef Cattle" National Academy Press, Washington, D.C., 1984, (6th ed.) pp. 40–44.

Goering, H.K. et al., 1970. "Forage Fiber Analyses" Agriculture Handbook No. 379. Jacket No. 387–598. Agricultural Research Service. United States Department of Agriculture, 1970, pp. 1–20.

Feng, P. et al., 1992. "Effect of Enzyme Additives on in situ and in vitro Degradation of Mature Cool–Season Grass Forage" J. Anim. Sci., 1992, 70 (Suppl.1):309.

Feng, P. et al., 1992. "Effect of Enzyme Additives to Cool–Season Grass Forage on Voluntary Intake and Digestive Function in Mature Beef Steers" J. Anim. Sci., 1992, 70 (Suppl. 1):310.

(List continued on next page.)

*Primary Examiner*—Neil S. Levy
*Attorney, Agent, or Firm*—Greenlee, Winner and Sullivan, P.C.

[57] ABSTRACT

Fibrolytic enzyme supplements for increasing the digestibility of legume forages and grain feeds for ruminants, a method of treating legume forages and grain feeds with fibrolytic enzymes, and feed compositions consisting of feed materials treated with a mixture of fibrolytic enzymes are provided. The enzyme supplements do not pre-digest the feed material but assist in the colonization of feed particles in the rumen by ruminal microbes. The fibrolytic enzyme supplements consist of mixtures of cellulase and xylanase in certain preferred ratios and levels which are dependent on the feed material to be treated. The cellulase and xylanase are dissolved in a buffer solution and sprayed onto dry legume forages or grain feeds. The feed material is then incubated for at least three hours to allow the enzymes to be absorbed into and adhere to the feed material. The resulting feed compositions remain stable for at least one year against predigestion. When cellulase and xylanase are applied to legume forages and grain feeds in certain ratios, levels and in accordance with the methods of the present invention, synergistic effects between the enzymes occur, providing large improvements in digestibility of feed materials at low enzyme levels.

21 Claims, 3 Drawing Sheets

OTHER PUBLICATIONS

Chesson, A., 1994. "Manipulation of Fibre Degradation—An Old Theme Revisited" T.P. Lyons and K.A. Jacques (Eds.). Biotechnology in the Feed Industry. Nottingham University Press. Loughborough, UK., 1994, pp. 83–98.

McAllister, T. A. et al., 1994. "A Review of the Microbial Digestion of Feed Particles in the Rumen" Asian J. Animal Sci., 1994, 7 (No. 3):303–316.

Gilbert, H.J. et al., 1992. "Homologous Catalytic Domains in a Rumen Fungal Xylanase: Evidence for Gene Duplication and Prokaryotic Origin" Molec. Microbiology, 1992, 6(15):2065–2072.

Van Soest, P.J., 1982. "Nutritional Ecology of the Ruminant" O&B Books. Corvallis, OR, 1982, pp. 23–38 and pp. 75–117.

National Research Council, 1982. "United States–Canadian Tabels of Feed Composition" National Academy Press, Washington, D.C., 1982, pp. 8–10 and pp. 49–50.

Nelson, C. J. et al, 1994. "Plant Factors Affecting Forage Quality" G.C. Fahey (ed.) Forage Quality and Utilization. American Society of Agronomy Inc., Madison, WI., 1994, pp. 115–154.

Berge, L.L. et al., 1994. "Modification of Forage Quality After Harvest" G.C. Fahey (ed.) forage Quality and Utilization. American Society of Argonomy Inc., Madison, WI., 1994, pp. 922–966.

5,720,971

ENZYME ADDITIVES FOR RUMINANT FEEDS

FIELD OF THE INVENTION

This invention relates to ruminant feed compositions containing xylanase and cellulase.

BACKGROUND OF THE INVENTION

Legume forages and grain feeds are common feedstuffs for ruminant animals. Though both legume forages and grain feeds contain a higher component of digestible matter than grass forages, both legume forages and grain feeds contain a significant partially-digestible or difficult to digest fraction, principally made up of plant cell walls. The cell wall component of the feed stuff is often described as the total fiber fraction.

Legume forages contain up to as much as 40% total fiber. The total fiber component of grain feeds is generally up to 20% of the total dry matter of the feedstuff (Van Soest, 1982). The remainder of the dry matter of the feedstuff is principally made up of non-structural carbohydrates which are readily digestible by ruminants. In both grain feeds and legume forages, the non-structural carbohydrate component of the feed is 90 to 100% digestible or convertible to energy resulting in animal growth. In grain feeds the total fiber component is only about 25% digestible whereas in legume feeds, the total fiber component is about 40% digestible (Van Soest, 1982).

The cell wall, or total fiber fraction of legume forages or grain feeds is principally cellulose, hemicellulose and lignin that are resistant to degradation. Although ruminants do not themselves secrete enzymes capable of digesting these substances, bacteria and fungi in the rumen produce enzymes capable of degrading cell wall substances. The extent of ruminal fiber digestion is variable and is dependent upon the type of feedstuff and the fibrolytic activity of ruminal microorganisms. The cellulose and hemicellulose components of the total fiber of legume forages and grain feeds are digestible by cellulase and xylanase produced by the ruminal bacteria. Digestibility of hemicellulose and cellulose is dependent upon, among other things, the degree and nature of association of the hemicellulose and cellulose with indigestible lignins. Cellulase and xylanase solubilize cellulose and hemicellulose to sugars which are in turn metabolized by rumen bacteria to the volatile fatty acids which the ruminant animal can use as a direct energy source. In the case of high-fiber forages, less than half of the forage may be digested and the undigested portion is excreted. This results in the production of large quantities of manure.

Improvements in feed digestibility are desirable as they result in faster animal growth and reduced manure output. As the non-structural carbohydrate fraction of legume forages and grain feeds is already highly digestible, there is little room for improvement. The greatest opportunities for improving feed digestibility therefore will result from increasing the digestibility of the less digestible total fiber fraction. There are currently no licensed feed additives that enhance the digestibility of fibrous feeds for ruminants.

The delivery of enzymes capable of degrading plant cell wall materials to the rumen is a difficult problem due to the highly proteolytic ruminal environment. If fibrolytic enzymes such as cellulase and xylanase, which are themselves proteins, are simply applied to feed stuffs, the fibrolytic enzymes are rapidly digested in the rumen before they can increase the fiber digestion of the ingested feedstuff (Chesson, 1994, McAllister et al., 1994). Direct addition of fibrolytic enzymes to the ruminal environment is also unlikely to be of benefit as the rumen contains bacteria, fungi and protozoa which produce the most active cellulase and xylanase known to exist in any environment (Gilbert, 1992). Any benefit of feeding fibrolytic enzymes to ruminants would therefore only be expected to be realized when extremely high levels of enzymes are used. Only at a very high enzyme level would the small proportion of added enzymes that were not rapidly hydrolyzed be sufficient to augment the fibrolytic activity naturally occurring within the rumen. Such an approach would be impractical and uneconomical.

Predigestion of forages with enzymes has been utilized as a technique to preserve and enhance the nutritive value of forage during ensiling. PCT Application No. PCT/FI91/00118 (SSV-Development OY, filed Apr. 18, 1991) describes the addition of one or more fibrolytic enzymes selected from the group consisting of pectinase, cellulase, xylanase, amylase, arabinosidase, cutinase, lipase and esterase to wet herbage (moisture content 50–75%) at the time of ensiling. This results in predigestion of the plant cell wall and consequent enhancement of the acid producing capability of lactic acid bacteria. The pH of the forage is maintained in a range below 4 to 4.5, excluding the growth of harmful bacterial species. Similarly, German Patent Application No. DD296407 A5 describes the application of a mixture of fibrolytic enzymes to fresh herbage at the time of ensiling. Japanese Patent No. 6,075,238 teaches the addition of an enzyme/microbial inoculant to feeds having a high moisture content stored in vacuum packaging to enable microbial fermentation.

Pre-digestion of feedstuffs is undesirable due to the high moisture content (greater than 30%) of the feed required to allow enzymatic activity. Moist feeds are inherently unstable as they are prone to contamination and spoilage by mold growth. The increased weight of the feed due to the high moisture content makes transportation impractical and the excess moisture may require additional drying of the feed before processing. These limitations make pre-digestion of feed an undesirable approach for increasing feed digestibility. It would be advantageous to increase digestibility of feed stuffs while maintaining the feed at a low moisture content.

Techniques for protecting enzymes from gastric or ruminal inactivation are also known. Canadian Patent No. 1,322,159 (Ying, issued Sep. 14, 1993) teaches the coating and encapsulation of enzymes with an acid-insoluble polymer to allow passage of enzymes through the rumen. Similarly, an aminopolyamide resin coating is taught by U.S. Pat. No. 3,492,398 (Marco et al., issued Jan. 27, 1970).

A cellulase/xylanase feed additive derived from selected strains of fungi has been used to treat malabsorption syndrome in poultry (PCT Application No. PCT/DK90/00256 (Novo Nordisk A/S, filed Oct. 5, 1990)).

Attempts have been made, with limited success, to increase the digestibility of ruminant feed stuffs by the addition of fibrolytic enzymes directly to the feedstuff or in the form of an enzyme supplement fed together with the feedstuff. Most of the supplements described in the prior art require a number of processing steps, including moistening of the feed, thermal treatment, drying, and the addition of other additives and stabilizing agents. European Patent Application No. 88105409.2 (Suomen Sokeri Oy, filed Apr. 4, 1988) describes the addition of an undisclosed enzyme supplement to a livestock feed with a moisture content between 15–60% followed by combined hydrothermal and enzymatic treatment at a temperature below 100° C. The feed material is then dried to stabilize the enzymes and improve the keeping quality of the feed material.

U.S. Pat. No. 5,314,692 (Haarasilta et al., issued May 24, 1994) describes a thermostable enzyme pre-mix containing 1 to 60% total enzymes selected from the group comprising amylases, cellulase, hemicellulase, glucanases, lipases, proteinases, and the like, and 40 to 99% flour or other starch. The enzyme premix is pelleted and designed to be mixed with other feeds at concentrations of 0.01 to 0.05%. The enzyme premix is thermally stable and does not exhibit significant degradation of the enzymes at feed processing temperatures.

U.K. Patent Application No. 2,261,877 (Kyowa Hakko Kogyo Co. Ltd., filed Nov. 18, 1992) describes a concentrated animal feed additive containing a plant tissue-destruction enzyme and at least one essential amino acid, effective for increasing milk yield, improving milk quality, promoting growth, improving meat quality, and elevating breeding efficiency.

German Patent Application No. DD296407 A5 describes a process of growing specific strains of Penicillium species of fungi on a substrate of triticale grain. The process involves prehydrolysis at temperatures between 15° and 60° C. at a moisture content greater than 25%. The resulting enzyme complex contains cellulase, hemicellulase, amylase, pectinase, protease, and β-1,4 glucanase. The material is ground to provide a feed supplement.

Feng et al. (1992, No. 1) demonstrated that application of an unspecified "high level" of an enzyme mixture containing cellulase, xylanase and hemicellulase to dried mature grass forage increased in vitro dried matter (DM) and neutral detergent fiber (NDF) digestibility by 12 and 20 percent, respectively. A "lower" level of cellulase and hemicellulase increased in vitro DM digestibility by 8 percent. In situ DM and NDF digestibility were measured but the results were not reported, presumably because no effect was observed. The reference illustrates that a combination of three classes of enzymes were required at a "high" level to improve the digestibility of mature dried grass hay. The enzymes were added immediately prior to the in vitro and in situ digestion studies.

Feng et al. (1992, No. 2) teaches the application of a commercial enzyme mixture containing cellulase, hemicellulase and xylanase to dry mature grass hay immediately prior to feeding. Through personal communications with the authors, the inventors have determined that the enzyme mixture used was a commercial product called Grass-Zyme which, in addition to cellulase, hemicellulase and xylanase, includes other classes of enzymes such as glucose oxidase and amylase. This pre-treatment increased hay DM intake by 12% relative to untreated hay. Digestibility of DM and NDF was also improved by enzyme pre-treatment. In situ NDF digestion rate was increased by pre-treating dry hay with the enzyme mixture immediately prior to feeding. When untreated hay was incubated in situ in the rumen of steers consuming pre-treated hay, no benefit was observed. These results suggests that the enzyme pre-treatment resulted in a partial digestion of the grass hay prior to ingestion rather than an increase in ruminal enzyme activity.

In light of the prior art, it is apparent that there remains a need for an enzymatic supplement for enhancing the digestibility of grain and legume feeds for ruminants. Such a supplement should be easy to apply to feeds, and not require complex, costly, or time consuming processing steps. Ideally, such an additive could be added to feed either near to the time of feeding, or at some earlier time, to allow processing of the feed into commercially acceptable forms. Such a supplement should therefore not pre-digest or hydrolyze the feed, but form a stable complex with the feed, allowing preservation and storage of the feed composition. The supplement should optimize forage digestibility at low or moderate enzyme levels in order to be practical and economical.

SUMMARY OF THE INVENTION

The inventors have discovered that when specific ratios and activity levels of fiber degrading enzymes, namely cellulase and xylanase enzymes, ere used to treat legume forages or grain feeds (feed material) by a method discovered by the inventors, surprising increases in feed material digestibility and animal growth result. Superior results are achieved when amounts of enzymes within certain preferred ranges are utilized than if excess amounts of enzymes are applied. An unexpected synergistic effect between the activities of the xylanase and cellulase on improving feed material digestibility and animal growth has been demonstrated as the improvements in feed material digestibility and animal growth resulting from application of the enzyme compositions of the present invention are greater than the simple additive improvement of xylanase and cellulase applied separately. The superior, synergistic results are not observed when the enzyme mixture of the present invention are applied to the feed material by a method other than that discovered by the inventors.

The present invention provides a method of incorporating a mixture of fiber-degrading enzymes into dry, processed or unprocessed feed materials to produce a stable feed composition for ruminants. This method enhances digestibility of feed materials when fed to ruminants. The invention extends to enzyme supplements containing specific mixtures of fiber degrading enzymes and feed compositions produced by treating forages with the enzyme supplements in accordance with the method of the present invention. As used herein "ruminants" includes cattle, sheep, goats, deer, bison, water buffalo and camels. Increased digestibility of the feed material results in increased animal performance characterized by improved rate of gain and milk yield, more efficient conversion of feed energy to meat or milk, less feed required to maintain the same level of productivity, greater feed intake achieved by animals requiring greater energy intake, decreased need for supplemental energy sources such as grains and fats, and reduced manure production.

In one preferred embodiment, the enzymes of the present invention are dissolved in aqueous solution and applied to dry feed material at the time of feed processing. The enzymes may be applied as separate solutions or may be applied as a single solution containing a mixture of enzymes. Preferably, the aqueous solution is a weak buffer having a pH between 4.5 and 7.0. The aqueous enzyme solution is applied to the feed material to coat the feed material and to provide an even distribution of the aqueous solution over the feed material. Typically, the enzyme solution will be sprayed onto the feed material while the feed material is simultaneously mixed to encourage an even distribution of the enzyme solution. The enzymes do not hydrolyze or predigest the feed material but adhere to the feed material, forming a stable enzyme/feed complex (feed composition). The enzymes will only adhere to the feed material if the feed material is sufficiently dry to allow substantial absorbtion of the aqueous solution containing the dissolved enzymes into the feed material. It has been determined that the feed material should have a moisture content preferably below 15% (w/w) for proper absorbtion to occur. Moisture occupies space in feedstuffs. As the moisture evaporates, pores are formed in the feedstuff into which the enzyme supplements of the present invention are absorbed, thereby taking the place of the evaporated moisture. If the moisture content of the feedstuff is substantially above 15%, the enzyme supplement will not be absorbed into the feedstuff. Further, if the moisture content of the feedstuff is maintained above about 18–20%, it is susceptible to mold damage. Field dried legume forages or grain feeds typically have moisture contents of about 12%. Absorbtion of the aqueous enzyme solution and formation of the stable enzyme/feed complex requires incubation of the feed material with the aqueous enzyme solution at temperatures between 5° and 80° C. for at least 3 hours, more preferably at least 8 hours. The resulting enzyme/feed complex is stable for up to at least one year. The feed material may be processed before or after treatment by rolling, chopping, tempering, grinding, cracking, popping, extruding, micronizing, roasting, flaking, cooking or exploding, or processed after treatment by pelleting, cubing or baling. Feed materials include legume hays, crop residues, and cereal grains.

The enzyme supplement includes cellulase and xylanase in certain preferred ratios and concentrations. It may also include pectinases, osterases, arabinosidases, and β-1,3 glucanases, but it does not require proteases, lipases or amylases. The cellulase and xylanase may consist of any broad spectrum cellulase and xylanase, preferably from microbial sources, applied at standardized activity levels. The activity of cellulase is standardized on the basis of filter paper degradation, expressed in filter paper unit (FPU) activity (µmoles glucose produced from filter paper per unit enzyme per minute). Xylanase activity is based on the hydrolysis of oat spelts xylan into xylose and expressed in international units (IU) (µmoles reducing sugars produced per unit enzyme per ml per minute). Assays for determining cellulase and xylanase activity are set forth in Examples 6, 7 and 8. The activity of cellulase, as discussed above, refers to exo-cellulases, and is measured in FPUs. Endo-cellulases, which may also be suitable for use as cellulases in accordance with the present invention, are measured in IUs as set forth in Example 7. 25 IU of endo-cellulase activity is equivalent to 1 FPU exocellulase activity.

The described method of producing a feed composition is most effective when cellulase and xylanase are provided in the feed composition in quantities sufficient to provide a ratio of cellulase activity to xylanase activity of between about 2 and 5 FPU cellulase per 100 IU xylanase to maximize feed digestibility and animal performance.

The inventors discovered that the increase in fiber digestion and animal performance depends on both the total amount of enzymes added to the feed material (expressed as total enzyme activity per kg feed dry matter) and the relative proportion of cellulase to xylanase. The relationship between enzyme concentration and animal response was found to be non-linear and is different for legume forages and grain feeds. For legume forages, such as alfalfa hay, an enzyme concentration of from 16 to 120 more preferably 18 to 72 FPU cellulase and from 800 to 6000 more preferably 900 to 3600 IU xylanase per kg of feed dry matter maximizes performance. For grain feeds, maximum performance of animals is obtained with enzyme concentrations from 10 to 200, and more preferably from 40 to 160 FPU cellulase and from 500 to 10,000 and more preferably 2000 to 8000 IU xylanase per kg of feed dry matter. For both legume forages and grain feeds, the ratio of cellulase activity to xylanase activity is preferably from 2 to 5 FPU cellulase per 100 IU xylanase.

In another broad aspect, this invention extends to particular ruminant feed compositions. Broadly, the feed compositions consist of low-moisture content feed material intimately associated with a mixture of cellulase and xylanase to provide a stable feed/enzyme complex. The ratio of cellulase activity to xylanase activity in the feed composition is preferably from 2 to 5 FPU cellulase per 100 IU xylanase. In one preferred embodiment, the feed composition is a stable enzyme/feed complex in which the enzymes provide from 60 to 120, more preferably 18 to 72, FPU cellulase activity and from 800 to 6,000, more preferably 900 to 3600 IU xylanase activity per kg of feed material, and in which the feed material is a dry legume forage. In another preferred embodiment, the feed composition is a stable enzyme/feed complex in which the enzymes provide from 10 to 200, and more preferably from 40 to 160 FPU cellulase activity and from 500 to 10,000, and more preferably 2000 to 8000 IU xylanase activity per kg of feed material, and in which the feed material is a dry grain feed. These feed compositions can be in cubed, pelleted, chopped, baled, rolled, tempered, ground, cracked, popped, extruded, micronized, roasted, flaked cooked or exploded form.

In yet a further embodiment, the invention provides an enzyme supplement for use in the aforementioned methods and feed compositions. The enzyme supplement is a mixture of cellulase and xylanase wherein the enzymes are included in amounts such that the ratio of cellulase activity to xylanase activity is from 2 to 5 FPU cellulase per 100 IU xylanase. The enzyme supplement may be dissolved in an aqueous solution for application to feed materials. Preferably the aqueous solution is a weak buffer having a pH between 4.5 and 7.0.

Without being bound by same, the inventors believe that the mechanism by which the present invention causes a synergistic relationship between the xylanase and cellulase provided in the enzyme supplements does not result from the simple fibrolytic activity of those enzymes. Improvements in feed conversion ratio (dry matter intake (DMI)/average daily gain/(ADG)) demonstrated in the Examples herein were too great relative to the proportionately small amounts of total fiber contained in legume forages and grain feeds to be attributed to the low levels of enzyme activity applied.

One might expect improvements in feed digestibility if high enzyme levels were applied to grass forages (as in the Feng et al. references). Grass hays such as those tested by Feng et al. are higher in total fiber than legume forages or grain foods. Approximately 50% of total fiber in grass hays is hemicellulose (i.e. xylan). The remaining 50% of the total fiber is lignin and cellulose (van Soest, 1982). For example, sun cured timothy hay (International Reference No. 1-04-885) contains 70% total fiber comprising 29% hemicellulose and 34% cellulose (National Research Council, 1982).

As set out above, the fiber composition of legume forages and grain feeds differs from that of grass hays. Legume forages such as alfalfa (International Reference No. 1-00-068) contain 50% total fiber, made up of 11% hemicellulose and 28% cellulose. As legume forages contain proportionally less hemicellulose than grass hays, it is unexpected that supplementation of a legume forage with cellulase and xylanase would significantly improve forage digestibility or growth rate in ruminants.

Similarly, grain feeds such as barley (International Reference No. 4-00-549) contain relatively small amounts of fiber (19% total fiber of which 5% is hemicellulose) and they are digested very rapidly in the rumen. Ruminants consuming diets high in grain feeds would not be expected to benefit significantly from enzyme supplementation.

Grass forages differ from legume forages and grain feeds both in morphological structure and chemical composition (Nelson et al., 1994). Leaves of grasses provide both structural and metabolic functions whereas in legumes, leaves provide only a metabolic function. The morphological structure of grain feeds is very different than grass hays in that the relatively small amounts of fiber in grains are located in the hull and surround the starchy endosperm.

Methods of pre-treatment that improve the nutritive value of grass hays are not effective in improving the nutritive value of legume forages. For example, in 24 studies with monocot (grass) crop residues, DM intake was increased by 22% as a result of sodium hydroxide treatment whereas in two studies of dicot (legume) crop residues, DM intake was increased by only 6% (Berger et al., 1994).

The cellulose composition of grasses and legume forages is generally similar. However, relative to legume forages, the celluloses of grasses have a high concentration of xylan-lignin bonds. In legume forages, the polysaccharides (xylan and cellulose) and lignins are more discretely compartmentalized. As a result, lignin acts as a greater physical barrier to fiber digestion in legume forages than in grasses. Further differences in fiber chemistry cause grasses to be more responsive to chemical treatment than legume forages. Enzymatic treatments that improve nutritive value of grass hay would not be expected to be effective in legume forages or grain feeds. The ratio of hemicelluse:cellulose in temperate grass forages ranges from 0.57 to 0.70 versus 0.32 to 0.40 in legumes. The major hemlcellulosic polysaccharides in legume forages are arabinoxylans, xyloglycans, arabinans and galactans, whereas the major hemicellulosic polysaccharides in grasses are xyloglucans and arabinoxylans. Xylose makes up 30% of sugars in grass hemicellulose and 20% of sugars in legume forage hemicellulose. As the hemicellulose of legume forages is a more complex mixture of sugars than the hemicellulose of grasses, a more complex regime of fibrolytic enzymes would be expected to be required for the degradation of legume forage hemicellulose.

As discussed previously, on the basis of prior art efforts, one would expect that very high levels of fibrolytic enzymes would be required to cause a substantial increase in feed material digestibility, particularly in legume forages and grain feeds having a lower total fiber content, as the rumen is a highly proteolytic environment and already has a highly evolved complement of microbes producing high-activity fibrolytic enzymes. Legume forages and grain feeds, providing relatively smaller proportions of total fiber, would be even less likely to show improvements in digestibility than grass forages.

Despite the foregoing, the inventors have demonstrated substantial improvements in legume forage and grain feed digestibility at relatively low enzyme addition levels. The feed conversion ratio observed for barley feed grain increased 12% (Table 3 in the Examples) suggesting a doubling in the digestibility of the total fiber component of the grain. The feed conversion ratio observed for alfalfa (a legume forage) increased 17% (9.92 kg feed/kg gain for untreated kay; 8.48 kg feed/kg gain for alfalfa hay treated with 3600 IU xylanase and 148 FPU cellulase per kg dry matter) indicating a substantial improvement of total fiber digestibility. These surprising improvements in digestibility should not have resulted from the simple additive enzymatic effects of the added cellulase and xylanase. Without being bound by same, the inventors believe that the enzyme supplements of the present invention create attachment sites for ruminal bacteria on treated feed particles thereby enhancing colonization and subsequent digestion of the feed particles by indigenous ruminal bacteria.

It is known that to be useful as feeds, plants must be resistant to microbial attack while growing in the field, but susceptible to penetration, colonization and digestion by microorganisms within the rumen. Protective barriers and substances that defend against microbial attack in the field (ie. waxy cuticle or phenolic acids) impede digestion of plant material within the rumen. Ruminal microorganisms circumvent these defenses through less resistant plant structures such as stomata or through disruption of the protective barriers due to chewing or mechanical processing (McAllister et al., 1994).

Once access is gained, rumen bacteria attach to inner tissues, form biofilms, and commence digestion. The initial colonizers release digestion products which in turn attract additional bacteria to the site of digestion forming a complex consortium of bacteria capable of digesting internal plant tissues. Thus, digestion of feeds in the rumen proceeds from within and the rate and degree of digestion of a feed material is often dictated by the extent to which ruminal microorganisms can access internal tissues (McAllister et al., 1994).

The enzyme supplements of the present invention are absorbed into the feed material where they are protected from solubilization in the proteolytic ruminal environment. The inventors believe that inside the feed material, the enzymes create attachment sites for initial colonization by ruminal microbes. It is further hypothesized that higher enzyme treatment levels are ineffective because the attachment sites formed are blocked by an excess of fibrolytic enzymes. The excess enzyme molecules bind over top of the attachment sites, creating a barrier to microbe attachment and activity.

The inventors' surprising discovery is of great utility as it allows improvements in total fiber digestibility to be made to feed materials which would otherwise be relatively insensitive to enzymatic treatment using cost effective quantities of enzymes at very specific ratios and activity levels applied in a simple and convenient method.

DETAILED DESCRIPTION OF PREFERRED EMBODIMENTS

Figure 1:
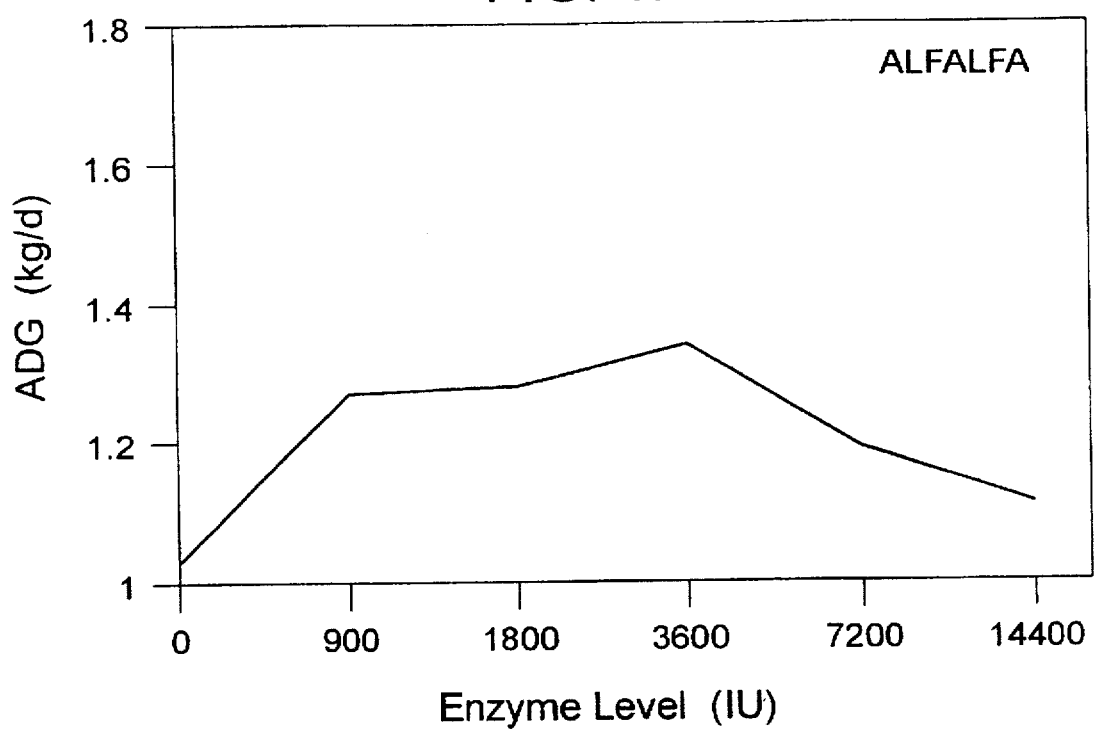
FIG. 1 is a graph plotting average daily gain (ADG) in kg per day of steers fed a diet of dry alfalfa forage as a function of enzyme activity level per kg feed material. Only the xylanase level is shown. The ratio of cellulase to xylanase activity was constant at 4 FPU cellulase activity per 100 IU xylanase activity.

The present invention provides enzyme supplements to improve the digestibility of dry legume forages and dried grain feeds when fed to ruminant animals and a method for treating legume forages and grain feeds with an enzyme supplement to form a stable enzyme/feed complex.

As used herein, the term "dry" as applied to a feed material, means a feed material having a moisture content of less than 15% (w/w).

As used herein, "legume forage" means the cut and cured aerial portion of a plant used as an animal feedstuff which is a dicotyledonous plant species that is a member of the botanical family Leguminosae. Examples include, without limitation, alfalfa, sainfoin, clovers and vetches. "Legume forages" includes forages comprising greater than 50% plant material from the Leguminosae family and up to 49% plant material of other species.

As used herein, "grain feeds" means the seeds of plants which are typically feed to ruminant animals which may or may not include the outer hull, pod or husk of the seed. Examples of grain feeds includes, without limitation, barley, wheat, corn, sorghum, triticale, rye, canola and soya beans.

As used herein, "cellulase" means an enzyme that solubilizes sugars from cellulase and "xylanase" means an enzyme that solubulizes sugars from hemicellulose.

As used herein, "feed material" means a legume forage or grain feed.

As used herein, "stable", as it is applied to feed compositions of the present invention, means that the xylanase and cellulase remain active and the feed material does not become moldy, rot, undergo pre-digestion or otherwise deteriorate for at least about one year after treatment.

As used herein, "coat" as it is applied to enzyme solution applied to feed materials means that the enzyme solution is distributed over the feed material substantially evenly. The coverage of the feed material with the enzyme solution may be discontinuous. However, on average, the distribution of the enzyme solution is substantially uniform.

The enzyme supplement includes cellulase and xylanase in certain preferred ratios and concentrations. It may also include pectinases, esterases, arabinosidases, and β-1-3 glucanases. No proteases, lipases or amylases are required.

It has been determined that the enzyme supplements are most effective in increasing feedstuff digestibility when the xylanase and cellulase are provided in preferred ratios of enzymatic activity and concentration. As used herein, "concentration" as it refers to the concentration of enzyme added to a feed material means the activity level of an enzyme per kg dry matter of a feed composition comprising a feed material treated with the enzyme supplement. The activity of cellulase is standardized on the basis of filter paper degradation, expressed in filter paper unit (FPU) activity (μmoles glucose produced from filter paper per unit enzyme per minute). Xylanase activity is based on the hydrolysis of oat spelts xylan into xylose and expressed in international units (IU) (μmoles reducing sugars produced per unit enzyme per ml per minute). Assays of cellulase and xylanase activity are set forth in the Examples.

When the cellulase and xylanase are present in the enzyme supplement within the preferred ratio and concentration ranges, a synergistic effect between the activities of the cellulase and xylanase on the digestibility of feed materials treated with the enzyme supplements is observed. The resulting improvements in digestibility is greater than that which would be predicted by simply adding the improvement to digestibility expected by treating feed materials with xylanase and cellulase applied separately. The synergistic effect is not noted when the cellulase and xylanase are provided in the enzyme supplement in ratios and concentration either below or above those of the present invention.

For legume forages, such as alfalfa hay, maximum improvement in digestibility of treated feed materials is observed when the cellulase and xylanase are present in the enzyme supplement in a ratio from 2 to 5 FPU cellulase per 100 IU xylanase. The preferred amount of cellulase and xylanase activity in the enzyme supplement is such that, when applied to a dry legume forage in accordance with the method of the present invention, from 16 to 120, more preferably 18 to 72, FPU cellulase activity and from 800 to 6000, more preferably 900 to 3600, IU xylanase activity per kg of feed dry matter is provided.

For grain feeds, the optimal cellulase to xylanase ratio is from 2 to 5 FPU cellulase per 100 xylanase. The enzyme supplement preferably contains sufficient amounts of the cellulase and xylanase to provide from 100 to 200, and more preferably from 40 to 60 FPU cellulase activity, and from 500 to 10,000 more preferably 2000 to 8000 IU xylanase activity per kg of feed dry matter.

To achieve the desired synergistic effects and improvement in digestibility of the feed materials, the cellulase and xylanase enzymes should be applied to the feed materials in accordance with certain procedures and parameters. Thus, the present invention extends to a method of treating a feed material with the enzymes to improve digestibility of the feed material. Improved digestibility and synergistic effect of the xylanase and cellulase is maximized where the enzymes are dissolved in an aqueous buffer solution between pH 4.5 and 7.0. The enzymes may be in separate solutions, more preferably in admixture, in one aqueous solution. The aqueous solution(s) is applied evenly to dry feed material having a moisture content of less than about 15%, at an ambient temperature between 5° and 80° C. The wetted feed material should then be incubated for at least 3 hours, more preferably at least 8 hours in order to stabilize the resulting feed/enzyme complex (feed composition).

Treatment of dry legume forages or grain feeds by the method of the present invention may be combined with various typical feed processing steps which may occur before or after enzymatic treatment. Such processing steps include, without limitation, tempering, popping, roasting, cooking or exploding the feed. When the processing step would result in compaction or densification of the feed in such a manner as to inhibit adsorption of the enzyme supplement into the feed material, enzyme treatment is preferably carried out prior to processing. Such processing steps would include, without limitation, pelleting, cubing or baling the feed. When the processing steps include high temperatures, the enzymes are preferably applied after processing.

Cellulase and xylanase used in accordance with the method of the present invention are available in either a powdered or liquid form. If in liquid form, the enzymes are preferably provided in aqueous solution, such as dissolved in an aqueous buffer solution at a pH in the range from 4.5 to 7.0. In accordance with the method of the present invention, a legume forage or feed grain is provided in a dried state, preferably having a moisture content of less than 15% (weight/weight). Field drying generally achieves that level of drying, although additional drying in grain dryers and the like may be necessary. With reference to the mass of the legume forage or feed grain, sufficient powdered or liquid xylanase and cellulase is diluted in water or a buffer solution to provide the desired ratio of cellulase to xylanase and the desired activity level of cellulase and xylanase per kg feed material. The enzymes may be added separately or may be supplied in a pre-mixed form at certain preferred ratios. The volume of water or buffer used to dilute the enzymes is not critical as long as not such a large volume is used as to raise the moisture content of the feed material above about 15–18%.

The dilute enzyme solution is then evenly applied such that it is distributed over the feed material (ie, by spraying). The treated feed composition thus formed is then incubated at a temperature preferably between 5° and 80° C. for at least about 3 hours, more preferably at least about 8 hours, to allow the enzymes to be absorbed into and adhere to the feed material, to allow excess moisture to evaporate, and to allow a stable feed/enzyme complex to form. The resulting feed composition should remain stable for at least one year.

Further specific embodiments and the utility of this invention are illustrated by the following non-limiting examples.

EXAMPLE 1

Application of Specific Ratios of Xylanase and Cellulase to Dry Legume Forages Results in Improved Animal Performance Seventy two growing steers, weighing 300 kg (ranging from 235 to 367 kg), housed in individual feeding pens, were allocated to three forage diets (24 animals/diet):

1. alfalfa hay cubes;
2. timothy hay cubes;
3. barley silage.

These forages were chosen to represent three types of forage diets: legume hay (alfalfa), grass hay (timothy) and grass silage (barley silage).

To each diet, graded levels of an aqueous mixture of commercial exocellulase (Spezyme CP, Genencor, Rochester, N.Y.) and xylanase (Xylanase B, Enzyme Development Corporation, New York, N.Y.) were added in a 3×6 factorial arrangement (3 diets×6 enzyme concentrations). Within each diet, 4 animals were allocated to each enzyme level (n=4). Enzymes were added to alfalfa and timothy hays during the cubing process at various levels (Table 1). The enzymes were applied to the forages for a minimum of 7 days prior to feeding. For barley silage, enzymes were added in the appropriate concentrations and mixed just prior to feeding. Protein/mineral supplements were added to each diet to provide a minimum of 12% crude protein, adequate rumen undegradable protein, Ca, P, and microminerals (NRC, 1984). Because the crude protein content of alfalfa cubes was substantially higher than that of timothy cubes or barley silage, the total crude protein intake of these animals was higher, but intake of rumen undegradable protein was similar. Animals were offered feed once a day at 1000 h. Feed allowance was 5 to 10% in excess of voluntary intake.

Animals were weighed at 0800 h in either 7 or 14-d intervals. Individual voluntary feed intake was determined throughout the experiment. Animals receiving hay cubes were hand-fed, animals receiving barley silage were fed using an automated feed mixer. Feed refusals were collected and weighed prior to feeding on every Mon, Wed, and Fri. Weekly refusal composites were dried at 55° C. for 72 h to determine dry matter (DM).

Average daily gain (ADG) was calculated from the live-weights by linear regression. Data were subjected to two-way analysis of variance with diet and enzyme addition as main effects. Because of consistent diet×enzyme interactions, enzyme effects were examined within each forage by one-way analyses of variance with enzyme addition as the main effect and initial weight as a covariate. The following non-orthogonal contrasts were tested: low enzyme levels (levels 1, 2 and 3) vs control and high enzyme level (level 5) vs all other enzyme levels (including control—zero enzyme).

The chemical composition of the forages is summarized in Table 2. Addition of fibrolytic enzymes slightly reduced NDF and ADF of timothy cubes, but not alfalfa cubes, indicating partial fiber hydrolysis prior to ingestion or grass but not legume hay. Average daily gain was enhanced by enzyme addition for alfalfa (P=15) and timothy cubes (P=0.065), but not (P=0.67) for barley silage (Table 1). However, the dose response to enzyme addition was non-linear (see FIGS. 1, 2 and 3).

For alfalfa, a legume forage, ADG increased with low levels of fibrolytic enzymes. High levels of fibrolytic enzymes were ineffective. The maximum response in ADG was observed at 3,600 IU xylanase/kg DM (FIG. 1). The ADG at this level was significantly higher (P=0.021) than that of control (1.34 vs 1.03 kg/d), but was similar (P=0.57) to ADG at lower enzyme levels. When contrasted together against the control, the three low enzyme concentrations increased (P=0.015) ADG.

Figure 2:
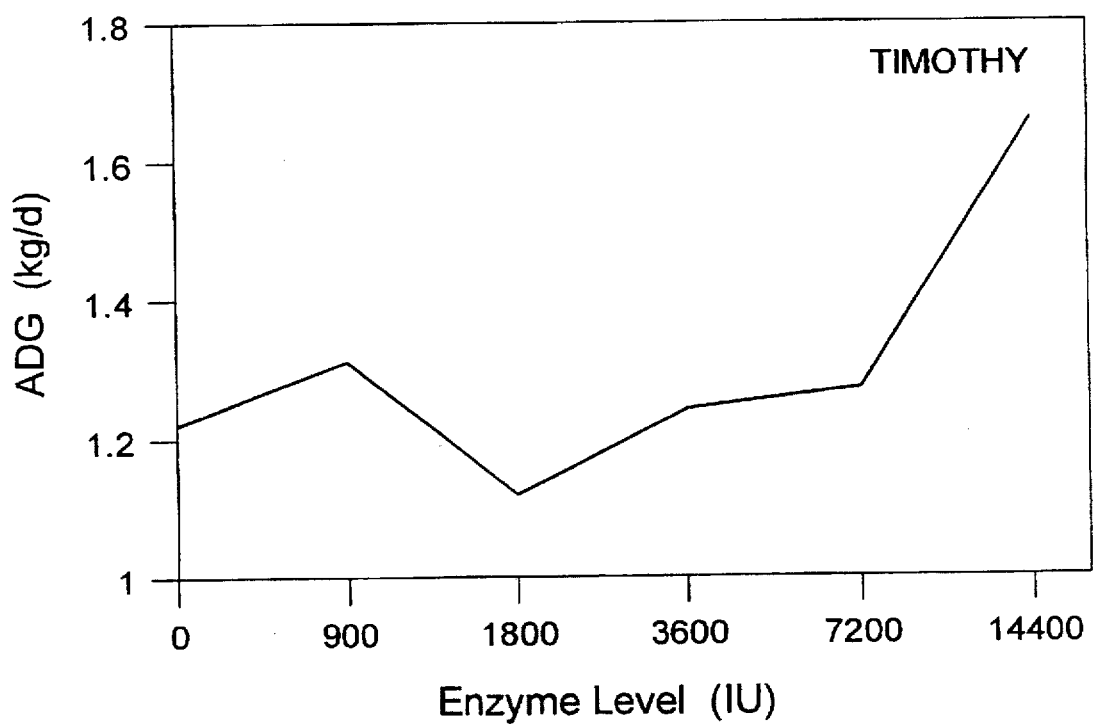
FIG. 2 is a graph plotting average daily gain (ADG) in kg per day of steers fed a diet of dry timothy forage as a function of enzyme activity level per kg feed material. Only the xylanase level is shown. The ratio of cellulase to xylanase activity was constant at 4 FPU cellulase activity per 100 IU xylanase activity.

For timothy, a grass forage, the maximum response in ADG was obtained at the highest enzyme concentration (12,000 IU xylanase/kg DM) (FIG. 2). The ADG at this level (1.66 kg/d) was higher (P<0.01) than for control (1.22 kg/d) and all lower enzyme levels. The results for timothy hay are consistent with those observed in the prior art.

Figure 3:
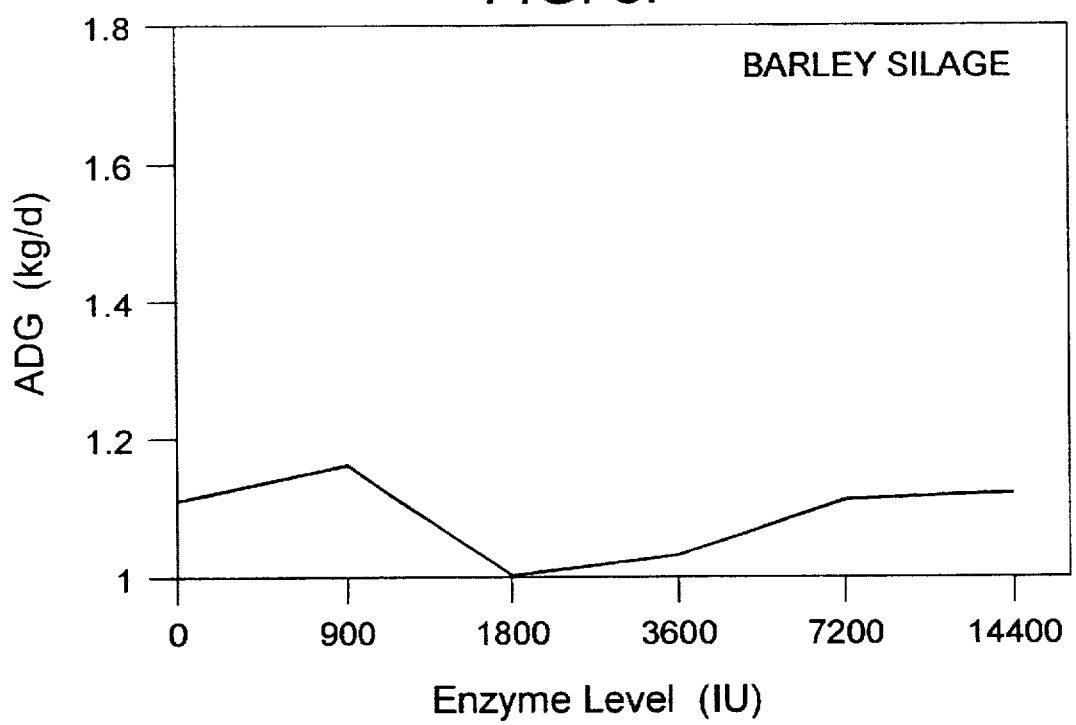
FIG. 3 is a graph plotting average daily gain (ADG) in kg per day of steers fed a diet of dry barley silage as a function of enzyme activity level per kg feed material. Only the xylanase level is shown. The ratio of cellulase to xylanase activity was constant at 4 FPU cellulase activity per 100 IU xylanase activity.

As expected, DM intake ("DMI") differed (P<0.001) considerably among forages (Table 1) and was lowest for barley silage and highest for alfalfa. Enzyme additives did not affect DMI of alfalfa (P=0.60) or barley silage (P=0.23). For timothy, animals receiving the highest concentration of enzymes had higher (P=0.043) DMI than that of control and all other enzyme levels. In contrast, animals fed barley silage did not benefit from fibrolytic enzymes added just prior to feeding (FIG. 3).

TABLE 1

Effect of enzyme level on average daily gain (ADG; kg/d) and dry matter intake (DMI; kg/d) in steers consuming different forages.

| | Forage | | | | | |
|---|---|---|---|---|---|---|
| | Alfalfa | | Timothy | | Barley silage | |
| Enzyme levels | ADG | DMI | ADG | DMI | ADG | DMI |
| 0 | 1.03 | 10.2 | 1.22 | 8.8 | 1.11 | 7.4 |
| 900 IU* 37 FPU** | 1.27 | 10.8 | 1.31 | 8.3 | 1.16 | 8.2 |
| 1,800 IU 74 FPU | 1.28 | 10.6 | 1.12 | 7.5 | 0.99 | 6.8 |
| 3,600 IU 148 FPU | 1.34 | 11.5 | 1.24 | 9.3 | 1.03 | 7.9 |
| 7,200 IU 296 FPU | 1.19 | 11.1 | 1.27 | 8.6 | 1.11 | 7.0 |
| 14,400 IU 592 FPU | 1.11 | 10.3 | 1.66 | 9.4 | 1.12 | 7.4 |

*IU = International units of xylanase/kg dry matter;
**FPU = filter paper units of cellulase/kg DM

TABLE 2

Acid detergent fiber (ADF) and neutral detergent fiber (NDF) in alfalfa and timothy treated with different enzyme levels.

| Enzyme level | Alfalfa | | Timothy | |
|---|---|---|---|---|
| per kg dry matter | ADF (%) | NDF (%) | ADF (%) | NDF (%) |
| 0 | 29.8 ± 1.0 | 44.7 ± 1.6 | 28.2 ± 0.3 | 55.0 ± 1.1 |
| 1,800 IU xylanase 74 FPU cellulase | 32.2 ± .03 | 44.1 ± 0.1 | 26.3 ± 0.0 | 53.6 ± 0.1 |
| 14,400 IU xylanase 592 FPU cellulase | 28.4 ± 3.0 | 42.6 ± 4.0 | 26.0 ± 0.5 | 52.8 ± 0.8 |

TABLE 3

Average daily gain in feedlot steers consuming diets containing 93% barley grain (DM basis) treated with fibrolytic enzymes.

| Treatment | Average daily gain (kg/d) | Feed efficiency kg feed/kg gain |
|---|---|---|
| 0 | 1.43 | 7.11 |
| 6,000 IU* 200 FPU** | 1.52 | 6.33 |
| 2,400 IU 420 FPU | 1.40 | 7.13 |

*IU = International units xylanase/kg DM;
**FPU = filter paper units cellulase/kg DM.

EXAMPLE 2

Application of Specific Ratios of Xylanase and Cellulase to Dry Grain Feeds Results in Improved Animal Performance Nineteen steers weighing 410 kg, were housed in individual feeding pens, were allocated to three feedlot diets:

1. Barley grain—no enzyme;
2. Barley grain with 6,000 IU xylanase and 200 FPU cellulase/kg DM.
3. Barley grain with 2,400 IU xylanase and 420 FPU cellulase/kg DM.

Diets consisted of 93% barley concentrate and 7% barley silage (DM basis). Aqueous mixtures of commercial exocellulase (Spezyme CP, Genencor, Rochester, N.Y.) and xylanase (Xylanase B, Enzyme Development Corporation, New York, N.Y.) were added to dry barley grain at least 24 hours prior to feeding. Barley grain was steam rolled and subsequently mixed with the barley silage just prior to feeding. Protein/mineral supplements were added to each diet to provide a minimum of 12% crude protein, adequate rumen undegradable protein, Ca, P, and microminerals (NRC, 1984). Animals were offered feed once a day at 1000 h. Feed allowance was 5 to 10% in excess of voluntary intake.

Animals were weighed at 0800 h in either 7 or 14-d intervals. Individual voluntary feed intake was determined throughout the experiment. Animals receiving hay cubes were hand-fed, animals receiving barley silage were fed using an automated feed mixer. Feed refusals were collected and weighed prior to feeding on every Mon, Wed, and Fri. Weekly refusal composites were dried at 55° C. for 72 h to determine DM.

Average daily gain (ADG) was calculated from the liveweights by linear regression after 98 days of feeding. Data were subjected to one-way analysis of variance with enzyme addition as the main effect. Results (Table 3) show that supplementing enzymes to grain feeds increased average daily gain by 6.3% and feed conversion efficiency by 12.3% (P<0.05). Superior results were achieve with the 3.3 FPU cellulase:100 IU xylanase supplement than with the 17.5 FPU cellulase:100 IU xylanase supplement.

EXAMPLE 3

Specific Ratios of Xylanase and Cellulase Result in Improved Feed Digestion

Using Ratios other than these Results in No Improvement or Negative Effects on Digestibility In the first two of three experiments, in vitro neutral detergent fiber (NDF) disappearance of dried alfalfa hay was determined after 24 h of incubation. Oven-dried, ground alfalfa hay, samples were incubated in buffered ruminal fluid (20% rumen fluid, 80% buffer) to which fibrolytic enzymes were added as above. Total enzyme (endocellulase+xylanase) concentration was 6,000 IU/kg, with varying endocellulase: xylanase ratios (0:100, 25:75, 50:50, 75:25 and 100:0). In the second experiment, the same protocol was used except that different endocellulase:xylanase ratios were used (0:100, 5:95, 10:90, 15:85, 20:80, 25:75 and 100:0). In the third experiment, the same protocol was used except that Spezyme CP exocellulase was used instead of CEP endocellulase. Enzyme levels for this experiment are given in Table 5.

In all experiments, the ruminal buffer was the phosphate/bicarbonate buffer of Goering and Van Soest (1970). Macrominerals, microminerals, peptone, and reducing agents were added to the buffer and the buffer was bubbled with $CO_2$ until completely reduced before mixing with ruminal fluid. After 24 h incubation at 39° C., the tube contents were extracted for 1 h in boiling neutral detergent solution and the residue was dried overnight at 105° C. (Experiment 1) or after 24 h incubation at 39° C., the tube contents were filtered through pro-weighed crucibles and dried overnight at 105° C. to measure DM digestion. In vitro results were statistically examined using a two-way ANOVA with forage and enzyme treatment as main effects. Enzyme effects were separated by the contrast with the control (no enzyme) vs. enzymes (irrespective of ratio).

Experiments 1 and 2.

Figure 4:
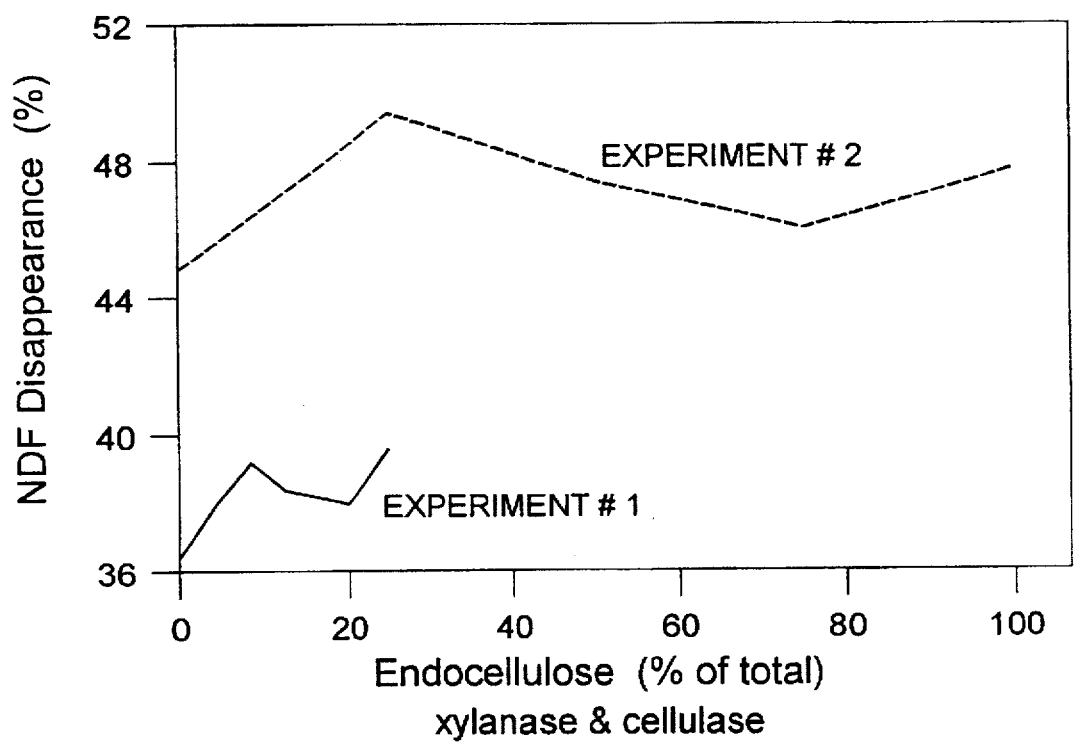
FIG. 4 is a graph plotting neutral detergent fiber (NDF) disappearance of dried alfalfa hay incubated in ruminal fluid as a function of the cellulase:xylanase activity ratio of the enzyme supplement at two sets of enzyme ratios.

Addition of fibrolytic enzymes significantly increased (P<0.01) NDF disappearance. Fiber disappearance increased with decreasing cellulase:xylanase ratio, with the response to the 25:75 cellulase:xylanase mixture greater (P<0.01; Table 4) than for other enzyme ratios. The application of xylanase enzyme alone was least effective in enhancing NDF disappearance with 100% cellulase being more effective. However, there was an associative synergistic effect between cellulase and xylanase application. While cellulase alone was more effective than xylanase alone, the combination of a small amount of cellulase (5 to 25% of total enzyme activity) resulted in the largest increase in NDF digestion (FIG. 4). Overall, a mixture of fibrolytic enzymes, with endocellulase comprising 25% and xylanase comprising 75% of total activity, resulted in an improvement or 26% and 8.2% in Experiments 1 and 2 respectively.

TABLE 4

Effect of xylanase and cellulase on in vitro NDF digestibility (24 hours) of alfalfa

| Cellulase (IU CMCase per kg DM) | Xylanase (IU per kg DM) | 24-hour digestibility (%) |
|---|---|---|
| 0 | 0 | 39.1 |
| 6,000 | 0 | 47.8 |
| 4,500 | 1,500 | 46.0 |
| 3,000 | 3,000 | 47.3 |
| 1,500 | 4,500 | 49.3 |
| 0 | 6,000 | 44.9 |

Experiment 3.

Figure 5:
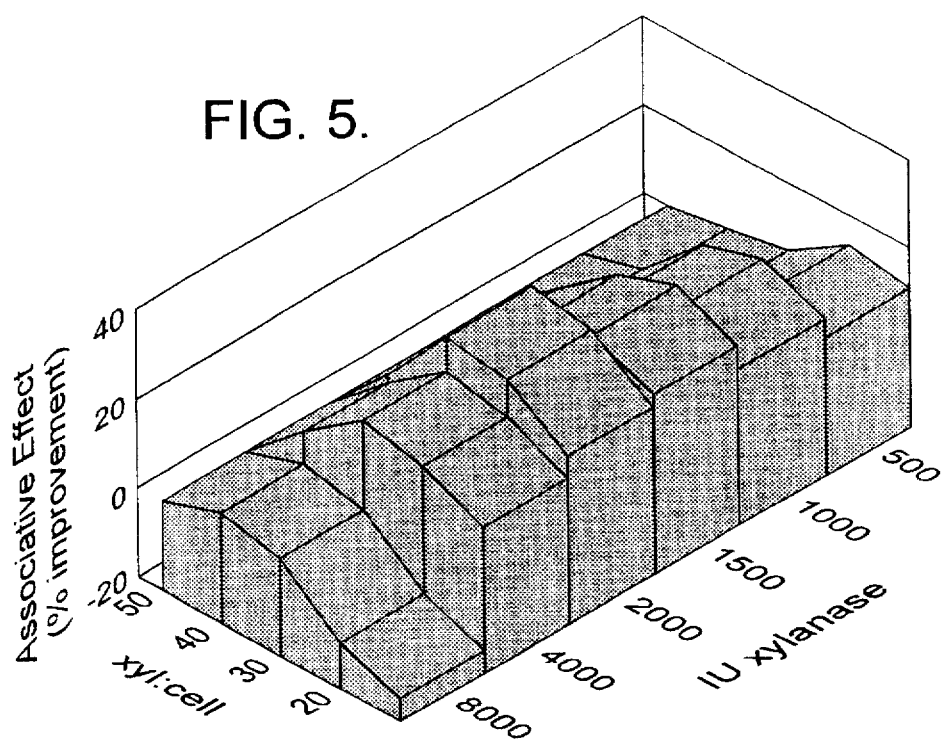
FIG. 5 is a three dimensional graph plotting NDF disappearance of dried alfalfa hay incubated in ruminal fluid as a function of both the cellulase:xylanase activity ratio of the enzyme supplement expressed as IU xylanase:1 FPU cellulase, and the level of enzymes added, expressed as IU xylanase activity per kg feed dry matter.

Results from this experiment further demonstrate the associative effect of xylanase and cellulase (Table 5 and FIG. 5). Methodology was identical to that used for Experiments 1 and 2 except that an exocellulase (Spezyme CP) was used. Ground alfalfa was incubated in vitro with different combinations and levels of xylanase and cellulase. Table 5; Column 4, contains values for DM digestion that were observed when xylanase alone was used. Column 5 contains values observed when cellulase alone was used. Column 6 contains the expected DM digestion that would be expected if xylanase and cellulase were additive in their effect on DM digestion of alfalfa (sum of the improvement in digestion observed from cellulase alone plus xylanase alone). Column 7 contains the actual observed DM digestion. The difference between observed and expected DM digestion (Column 8) expressed as a percent, is the change due to the action of cellulase and xylanase acting in an associative, synergistic manner.

As the level of xylanase and cellulase increased (FIG. 5 shows only the level of xylanase activity) the associative effect of the enzymes increased. Maximum associative effect occurred when xylanase was added at a level of 2,000 IU/kg DM. The associative effect was also influenced by the ratio of xylanase:cellulase. Maximum associative effect occurred when the ratio of xylanase:cellulase (IU:FPU) was between 30:1 and 40:1 (2.5 to 3.3 FPU cellulase per 100 IU xylanase). For example, applying 1,500 IU xylanase and 50 FPU cellulase per kg DM resulted in DM digestibilty of 63.1% compared to 40.1% for the untreated alfalfa, 43.98% for 1,500 IU xylanase/0 FPU cellulase and 45.6% for 0 IU xylanase/50 FPU cellulase treated alfalfa. Addition of high xylanase and cellulase activities actually depressed digestibility. For example, applying 8,000 IU xylanase and 400 FPU cellulase per kg DM (20:1 ratio) resulted in DM digestibilty of 53.4% compared to 40.1% for the untreated alfalfa, 44.05% for 8,000 IU xylanase/0 FPU cellulase and 54.3% for 0 IU xylanase/400 FPU cellulase treated alfalfa. These findings demonstrate that there is an optimum level and ratio of xylanase and cellulase to improve digestion of alfalfa. Using inappropriate ratios and levels outside of those specified will result in no response or even negative effects.

EXAMPLE 4

Enzymes must be Applied to Dry Feed Materials and must be Absorbed into and Adhere to the Feed Material Prior to Ingestion A minimum Length of Time to Stabilize the Enzyme-feed Complex is Required An experiment was conducted to determine the effects of adding a fibrolytic enzyme mixture to alfalfa silage on intake and digestibility of dry matter, and whether the enzyme mixture is equally effective on dry versus wet forage.

TABLE 5

Associative effect of adding combinations of xylanase and cellulase compared to adding individual enzymes on in vitro DM digestion of alfalfa.

| Xylanase IU/kg | Cellulase FPU/kg | Xylanase Cellulase Ratio | Expected % DMD from xylanase | Expected % DMD from cellulase | Expected total % DMD | Observed % DMD | % improve due to synergism |
|---|---|---|---|---|---|---|---|
| 0 | 0 | 0 | 0 | 0 | 40.11 | 40.11 | 0 |
| 500 | 10 | 50:1 | 41.19 | 42.37 | 43.45 | 45.02 | 3.9122851 |
| 500 | 12.5 | 40:1 | 41.19 | 42.45 | 43.53 | 46.45 | 7.2763519 |
| 500 | 16.66667 | 30:1 | 41.19 | 42.09 | 43.17 | 50.29 | 17.742337 |
| 500 | 25 | 20:1 | 41.19 | 43.56 | 44.64 | 51.62 | 17.393471 |
| 1000 | 20 | 50:1 | 42.44 | 44 | 46.33 | 48.86 | 6.3045103 |
| 1000 | 25 | 40:1 | 42.44 | 43.66 | 45.89 | 54.61 | 21.72938 |
| 1000 | 33.33333 | 30:1 | 42.44 | 44.87 | 47.2 | 58.09 | 27.136805 |
| 1000 | 50 | 20:1 | 42.44 | 45.6 | 47.93 | 57.61 | 24.121605 |
| 1500 | 30 | 50:1 | 43.98 | 44.09 | 47.96 | 53.82 | 14.602542 |
| 1500 | 37.5 | 40:1 | 43.98 | 44.67 | 48.54 | 59.11 | 26.339397 |
| 1500 | 50 | 30:1 | 43.98 | 45.6 | 49.47 | 63.14 | 34.064291 |
| 1500 | 75 | 20:1 | 43.98 | 47.54 | 51.41 | 63.25 | 29.504112 |
| 2000 | 40 | 50:1 | 44.79 | 45.31 | 49.99 | 56.85 | 17.094443 |
| 2000 | 50 | 40:1 | 44.79 | 45.6 | 50.28 | 64.95 | 36.556192 |
| 2000 | 66.66667 | 30:1 | 44.79 | 46.27 | 50.95 | 65.16 | 35.409918 |
| 2000 | 100 | 20:1 | 44.79 | 49.11 | 53.79 | 63.91 | 25.218041 |
| 4000 | 80 | 50:1 | 45.82 | 48.62 | 54.33 | 60.48 | 15.325193 |
| 4000 | 100 | 40:1 | 45.82 | 49.11 | 54.82 | 66.39 | 28.831298 |
| 4000 | 133.3333 | 30:1 | 45.82 | 50.24 | 55.95 | 66.53 | 26.364316 |
| 4000 | 200 | 20:1 | 45.82 | 51.32 | 57.03 | 64.71 | 19.137802 |
| 8000 | 160 | 50.1 | 44.05 | 50.65 | 54.59 | 56.77 | 5.4323449 |
| 8000 | 200 | 40:1 | 44.05 | 51.32 | 55.26 | 56.31 | 2.6164964 |
| 8000 | 266.6667 | 30:1 | 44.05 | 53.02 | 56.96 | 53.64 | −8.273112 |
| 8000 | 400 | 20:1 | 44.05 | 54.28 | 58.22 | 53.35 | −12.13556 |

Second-cut alfalfa was cut and preserved as silage using three small upright experimental silos each containing approximately 700 kg of silage. A portion of the silage was dried using a small-scale rotating drum drier constructed for experimental purposes by the Alberta Farm Machinery Research Institute in Lethbridge. Approximately 850 kg of wet silage (approximate dry matter content or 33%) was dried between 60° and 70° C. for approximately 6 to 8 hours to a moisture content of less than 15% in three different batches.

Five wethers were used in an experiment designed as a 5×5 modified Latin square with five 14-d experimental periods. The diets were allocated such that all sheep had received all diets by the end of the experiment. The five diets were: 1) alfalfa silage, 2) alfalfa silage with fibrolytic enzymes, 3) dried alfalfa silage, 4) dried alfalfa silage with fibrolytic enzymes, and 5) alfalfa silage cubes.

The fibrolytic enzyme mixture used in this study was a mixture of xylanase (Xylanase B, Enzyme Development Corporation, New York, N.Y.) and cellulase (Spezyme CP, Genencor, Rochester, N.Y.) applied at 3.75 international units (IU) of xylanase and 0.25 filter paper units (FPU) of cellulase per gram of feed dry matter. The enzyme mixture was applied at the time of feeding.

The wet alfalfa diets were offered during the first two periods to avoid spoilage. Feed was offered twice daily at 110% of voluntary intake. Feed refusals were collected daily and retained for chemical analyses to determine voluntary intake. Sheep were housed in collection crates during the last 10 d of each period to facilitate total daily collection of feces.

Data for daily dry matter intake and total dry matter digestibility of forage were analyzed using a general linear model with sheep and diet in the model. Period effects were not included in the model because diets were not truly randomized according to a Latin square design.

The effectiveness of added enzymes depended upon whether the silage was wet or dry. Addition of the enzyme mixture increased dry matter digestibility by 2.9% (63.1 vs. 61.3%; P<0.04; Table 6) in the case or dried silage, but had no effect on digestibility of wet silage. Animals fed dried silage consumed more than those fed wet silage, but enzyme addition had no effect (P>0.05) on dry matter intake. Intake of digestible dry matter was marginally increased due to enzyme addition.

These results indicate that the enzyme additive increases forage digestibility when applied in a manner allowing the enzymes to adhere to the substrate. In the case of dry silage, the liquid enzyme mixture was immediately absorbed when applied to the forage, whereas the high moisture content of the wet silage may have impeded absorption of the enzyme. The enzymes may have been solubilized from the wet forage more easily upon insalivation by the animal or upon contact with ruminal fluid.

In Example 1 wherein barley silage fed to cattle, enzymes applied prior to feeding had no effect on animal performance. In that study, enzymes applied to dry feed (i.e., timothy and alfalfa cubes) at the time of processing were effective. Both Example 1 and Example 4 indicate that enzymes must be applied to dry feed.

TABLE 6

Effect of fibrolytic enzymes on digestibility of alfalfa silage dry matter (DM)

| Alfalfa silage | Enzyme | Intake (kg/d) | | Digestibility (%) |
|---|---|---|---|---|
| | | DM | Digestible DM | |
| wet | − | 1.50 | .93 | 61.8 |
| | + | 1.58 | .97 | 61.8 |
| dry | − | 1.75 | 1.07 | 61.3 a |
| | + | 1.73 | 1.09 | 63.1 b | a,b Effect of enzyme added to dried silage was significant (P < .04).

EXAMPLE 5

The Enzyme/Feed Complex Requires a Minimum Incubation Period to Become Stable

An experiment was conducted to determine the effect of stabilization time for a fibrolytic enzyme mixture on digestibility of alfalfa hay.

Composite samples of dry alfalfa hay were ground to pass a 2 mm screen. A solution of fibrolytic enzymes consisting of xylanase (Xylanase B, Enzyme Development Corporation, New York, N.Y.), cellulase (Spezyme, Genencor, Rochester, N.Y.), and 10 mM acetate buffer (pH 4.8) was sprayed onto each feed. The solution was applied at the rate of 0.09g mL/g of feed (as-is basis). For alfalfa, 2,000 IU of xylanase and 67 FPU of cellulase were added per kg of dry matter. Enzymes were stabilized on the feed for 0, 0.5, 1, 2, 4, 6, 8, 12, 24 and 32 h. Treated forages were incubated in buffered (pH 6.8) ruminal fluid (20% rumen fluid, 80% buffer) according to the method of Goering and Van Soest (1970). Buffered ruminal fluid was added to the 0 h treatment within 5 min. of applying the enzyme solution. A final treatment consisted of adding the enzyme solution after ruminal fluid was added to the feed. At each stabilization time, a sample of forage without enzyme was incubated and used as a control for that stabilization time. These controls were needed to eliminate the variable nature of the rumen fluid inoculum among replicates. All incubations were conducted in triplicate for 24 h at 39° C. After incubation, samples were filtered to determine dry matter digestibility. Residues were analyzed for neutral detergent fiber (NDF) to determine fiber digestibility. Results for digestibility are reported as a percentage of the respective control incubation.

Figure 6:
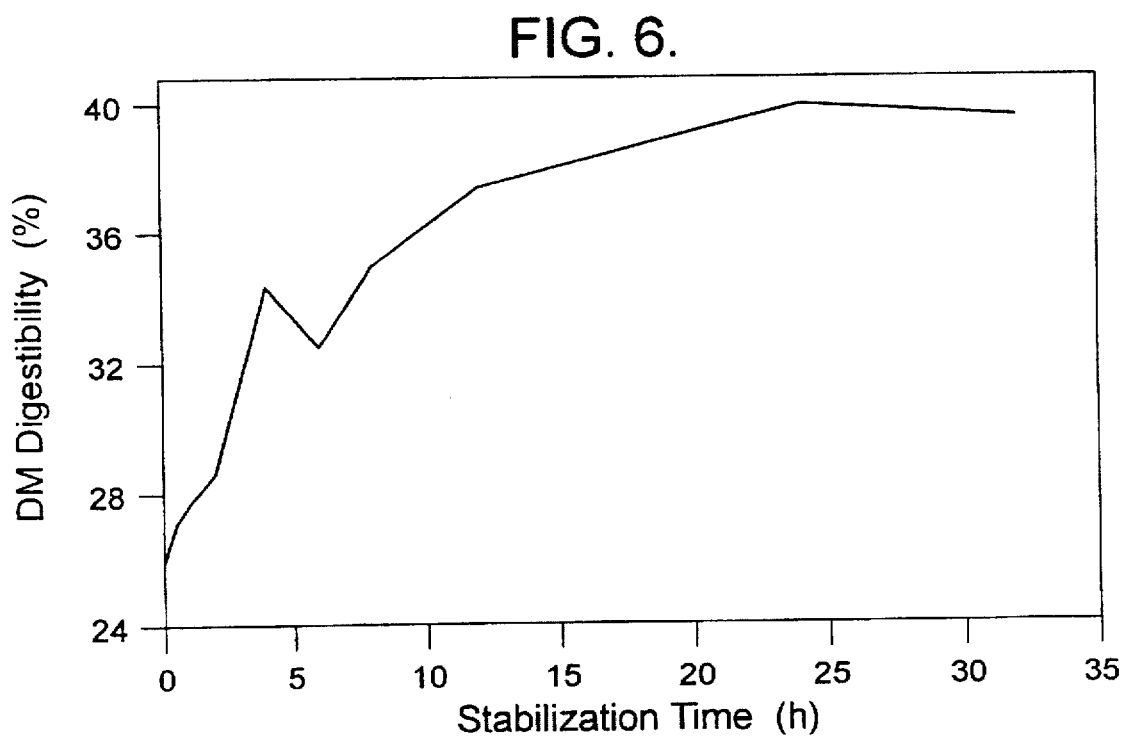
FIG. 6 is a graph plotting dry matter digestibility (NDF disappearance) of dried alfalfa hay incubated in ruminal fluid as a function of incubation time of the enzyme-treated alfalfa after enzyme treatment.

The results of this study are shown in FIG. 6. Dry matter disappearance increased above the untreated control at each increment of incubation time up to 24 hours. These results clearly demonstrate the need for a period so that the enzyme/feed complex can stabilize. For periods up to 2 hours there was a nominal increase in DM digestibility. Satisfactory stabilization was achieved within 3 hours. Most of the stabilization effect had been achieved by 8 hours with maximum stability and DM digestion occurring with 24 hours of stabilization. The alfalfa was dry so no predigestion was involved. The observed response was due to the binding of the enzyme to the feed and time was needed to form this stable complex.

EXAMPLE 6

Assay of Exo-Cellulase Activity Expressed in Filter Paper Units

Principle

The cellulase in the sample hydrolyzes the substrate, filter paper, and the reducing sugars thus released are assayed spectrophotometrically using dinitrosalicylic acid.

Unit of Activity

The unit of filter paper activity is FPU (see calculation)

| Assay Conditions | |
|---|---|
| Substrate | Filter Paper |
| pH | 4.8 |
| Incubation Temperature | 50° C. |
| Incubation Time | 60 min |
| Equipment | |
| Water Bath | 50° C. |
| Water Bath | 100° C. |
| Test Tube Mixer (vortex) | |
| Spectrophotometer | |

Reagents

All solutions are prepared in deionized water, Milli-Q or equivalent.
1. Citrate Buffer (0.05M, pH 4.8) Prepare 0.05M solutions of both citric acid ($C_8H_8O_7.H_2O$.10.51 g/l) and sodium citrate ($C_6H_5Na_3O_7$.14.71 g/l) in water. Adjust the pH of the 0.05M citrate solution to 4.8 with the 0.05M citric acid solution (should require about 667 ml of citric acid solution per 1 litre of sodium citrate solution).
2. Substrate Whatman No. 1 filter paper strip, 5 mm W×120 mm L (49.6–50.5 mg). Note: It is important that this weight be achieved and it can be done by snipping off the corner of the strip and weighing.
3. DNS reagent Dissolve 5.0 g of 2-hydroxy-3,5-dinitrobenzoic acid (also known as 3,5 dinitrosalicylic acid—Merck 800141) in about 4 liters of water. With continuous magnetic stirring, gradually add 8.0 g of NaOH and let it dissolve. Add 150 g of Rochelle Salt (Kna-tartrate, Merck 8087) in small portions with continuous stirring. The solution may be cautiously warmed to a maximum temperature of 45° C. Cool to room temperature and dilute with water to 500 ml in a volumetric flask. If the solution is not clear, filter through Whatman 1 filter paper. Store in a dark bottle at room temperature.
4. Glucose Standard Dissolve 1.00 g of glucose (Merck 8337; stored in desiccator) in citrate buffer and make the volume up to 250 ml in a volumetric flask. This solution contains 2.0 mg of glucose in 0.5 ml.

Sample

The sample is diluted in citrate buffer. At least two dilutions must be made of each enzyme sample investigated. One dilution should release slightly more and one slightly less (absolute amount) than 2.0 mg glucose (equivalent reducing sugars as glucose) in the reaction conditions.

Assay

Tightly wind into small curl the filter paper strip, place in the dry test tube (25 ml) and add 1.0 ml of citrate buffer using the pipette to keep the paper submerged. Equillbrate at 50° C. for 5 min. At time zero add 0.5 ml of sample to the test tube and mix (the strip must stay below the liquid surface). After exactly 60 min. incubation at 50° C. add 3.0 ml of DNS reagent and mix. Place all tubes (all samples, enzyme blanks, glucose standard and reagent bland) in a boiling water bath one at a time. After boiling for exactly 5 min., remove the tubes and cool to room temperature. Add 20 ml of water. Mix by completely inverting the tube several times. When the pulp has settled well, i.e., after at least 20 min., the solution is transferred to a cuvette with a pipette and the color formed is measured against the reagent blank at 540 nm.

| Enzyme blank | 1.0 ml buffer | Reagent blank | 1.5 ml buffer |
|---|---|---|---|
| | 0.5 ml sample | | 3.0 ml DNS |
| | 3.0 ml DNS | | |
| Glucose Standard | 1.0 ml buffer | | |
| | 0.5 ml standard | | |
| | 3.0 ml DNS | | |

Boil for 5 min., add 20 ml of water, etc. Measure the absorbance of the samples, enzyme blanks and glucose standard against the reagent at 540 nm.

Calculation

The unit of FPU is based on International Unit (Note: FPU assay is nonlinear, the use of international units per se is incorrect).

$1 \text{ IU} = 1 \text{ } \mu\text{mol min}^{-1}$ of substrate converted
$= 1 \text{ } \mu\text{mol min}^{-1}$ product formed (reducing sugars as glucose, the molecular weight of glucose is 180 g mol$^{-1}$)

The absolute amount of glucose released in the FPU assay at the critical dilution is 2.0 mg. This amount of glucose is produced by 0.5 ml enzyme in 60 min in the hydrolysis reaction and is equivalent to:

$$\frac{2.0 \text{ mg}}{0.18 \text{ mg } \mu\text{mol}^{-1} \cdot 0.5 \text{ ml} \cdot 60 \text{ min}} = 0.37 \text{ } \mu \text{ mol min}^{-1} \text{ ml}^{-1}$$

Plot the sample absorbance (after substraction of enzyme blanks) against enzyme dilution (total volume or dilution divided by the volume of enzyme in dilution) on a semi-logarithmic graph paper. Read the critical dilution for each sample corresponding to the absorbance of the standard.

FPU/ml=critical dilution 0.37

EXAMPLE 7

Assay of Endo-Cellulase (Carboxy-Methyl Cellulose) Activity Expressed in International Units Principle The CMCase in the sample hydrolyzes the substrate, carboxymethyl cellulose (CMC), and the reducing sugars thus released are assayed spectrophotometrically using dinitrosalicylic acid.

Unit of Activity

Units are expressed as International Units (IU). One IU of activity liberates 1 µmole of reducing sugars (expressed as glucose equivalents) in 1 minute under assay conditions.

| Assay Conditions | |
|---|---|
| Substrate | carboxymethyl cellulose |
| pH | 4.8 |
| Incubation Temperature | 50° C. |
| Incubation Time | 60 min |
| Equipment | |
| Water Bath | 50° C. |

| | |
|---|---|
| Water Bath | 100° C. |
| Test Tube Mixer (vortex) | |
| Spectrophotometer | |

Reagents

All solutions are prepared in deionized water, Milli-Q or equivalent.
1. Citrate Buffer (0.05M. pH 4.8) Prepare 0.05M solutions of both citric acid ($C_6H_8O_7 \cdot H_2O$. 10.51 g/l) and sodium citrate ($G_6H_6Na_3O_7 \cdot 2H_2O$, 14.71 g/l) in water. Adjust the pH of the 0.05M citrate solution to 4.8 with the 0.05M citric acid solution (should require about 667 ml of citric acid solution per 1 litre of sodium citrate solution).
2. Substrate—1% carboxymethyl cellulose Dissolve 1.0 g of CMC; medium viscosity (Sigma No. C-4888) into about 80 ml of 0.05M citrate buffer preferably using a heating magnetic stirrer. Heat to boiling point and cool with continued stirring, cover and stir slowly overnight. Make the volume up to 100 ml with the citrate buffer. Can be stored at 4° C. for a maximum of one week.
3. DNS reagent Dissolve 5.0 g of 2-hydroxy-3,5-dinitrobenzoic acid (also known as 3,5 dinitrosalicylic acid—Merck 800141) in about 4 litres of water. With continuous magnetic stirring, gradually add 8.0 g of NaOH and let it dissolve. Add 150 g of Rochelle Salt (Kna-tartrate, Merck 8087) in small portions with continuous stirring. The solution may be cautiously warned to a maximum temperature of 45° C. Cool to room temperature and dilute with water to 500 ml in a volumetric flask. If the solution is not clear, filter through Whatman 1 filter paper. Store in a dark bottle at room temperature.

Sample.

The sample is diluted in 0.05M sodium citrate buffer. A suitable dilution will yield an absorbance of 0.3–0.5.

Assay

Add 1.8 ml substrate solution to two test tubes and equilibrate at 50° C. for minutes. Add 200 µl of suitably diluted enzyme solution to one of the tubes and mix with the vortex mixer. After exactly 5 minutes at 50° C. add 3.0 ml DNS reagent to both tubes and mix. Add 200 µl of sample solution to the tube incubated without sample (enzyme blank). Place both tubes in a boiling water bath one at a time. After boiling for exactly 5 minutes remove the tubes and cool in cold water to room temperature. Measure the sample absorbance against that of the enzyme blank at 540 nm. Read the activity from the standard line and multiply by the dilution factor.

Standard

Prepare 0.01M stock solution of glucose by dissolving 0.180 g of glucose (Merck 8337; store in dessicator) into 100 ml of buffer. Stock solution can be frozen in small aliquots at −20° C.; after thawing the tubes must be carefully mixed. Make the following dilutions from the stock solution in citrate buffer:

| Dilution | Glucose µmol/ml |
|---|---|
| 1:1 | 10.0 |
| 1:2 | 5.0 |
| 1:4 | 2.5 |
| 1:5 | 2.0 |

Do triplicate assays of each standard dilution in the same way as the enzyme blank: pipette into test tubes 1.8 ml substrate, incubate 50 minutes at 5° C., add 3.0 ml DNS and 200 µl standard dilution. Prepare the reagent blank by adding 200 µl citrate buffer instead of the standard dilution. Boil the tubes exactly 5 minutes, cool and measure the absorbance against the reagent blank at 540 nm. Construct a standard line for every series of assays.

EXAMPLE 8

Assay of Xylanase Activity Expressed in International Units

Principle

Xylanase in the sample hydrolyzes the substrate, oat spelt xylan, and the amount of released reducing carbohydrates is determined spectrophotometrically using Odinltrosalicylic acid.

Unit of Activity

One xylanase unit (International Units; IU) is defined as the amount of enzyme that produces reducing carbohydrates having a reducing power corresponding to one µmole xylose (as reducing sugar equivalents) from oat spelt xylan in one minute under the assay conditions.

| Assay Conditions | |
|---|---|
| Substrate | oat spelt xylan |
| pH | 5.3 |
| Temperature | 50° C. ± 0.5° C. |
| Incubation time | 5 min. |
| Equipment | |
| Water bath | 50° C. |
| Water bath | 100° C. |
| Test tube mixer (vortex) | |
| Spectrophotometer | |

Reagents
1. 0.05M sodium citrate buffer, pH 5.3. Prepare 0.05M solutions of both citric acid and sodium citrate by weighing 10.5 g of citric acid ($C_6H_8O_7 \times H_2O$) into 1 litre of deionized water and 14.7 g of sodium citrate ($C_8H_5O_7Na_3 \times 2H_2O$) into 1 litre of deionized water. Citric acid solution is added to the sodium citrate solution unit the pH of the mixture is 5.3.
2. Substrate—1% oat spelt xylan Dissolve 1.0 g of xylan (Sigma No. X-0627) into about 80 ml of 0.05M citrate buffer preferably using a heating magnetic stirrer. Heat to boiling point and cool with continued stirring, cover and stir slowly overnight. Make the volume up to 100 ml with the citrate buffer. Can be stored at 4° C. for a maximum of one week.
3. DNS reagent Suspend 20.0 g 2-hydroxy-3,5-dinitrobenzoic acid (Merck 800141) in about 400 ml deionized water. With continuous magnetic stirring, gradually add to this suspension 300 ml of NaOH solution (32.0 g NaOH in 300 ml deionized water). The solution may be warmed cautiously in a water bath to a maximum temperature of 45° C. until it is completely clear. Add 600 g of Rochelle salt (Kna-tartrate, Merck 8087) in small portions with continuous stirring. Finally, dilute the solution with deionized water to 2000 ml. If the solution isn't clear, filter through a filter paper (Whatman No. 1). Store in a dark bottle at room temperature.

Sample

The sample is diluted in 0.05M sodium citrate buffer. A suitable dilution will yield an absorbance of 0.3–0.5.

Assay

Add 1.8 ml substrate solution to two test tubes and equilibrate at 50° C. for 5 minutes. Add 200 µl of suitably diluted enzyme solution to one of the tubes and mix with the vortex mixer. After exactly 5 minutes at 50° C. add 3.0 ml DNS reagent to both tubes and mix. Add 200 µl of sample solution to the tube incubated without sample (enzyme blank). Place both tubes in a boiling water bath one at a time. After boiling for exactly 5 minutes remove the tubes and cool in cold water to room temperature. Measure the sample absorbance against that of the enzyme blank at 540 nm. Read the activity from the standard line and multiply by the dilution factor.

Standard

Prepare 0.01M stock solution of xylose by dissolving 0.150 g of xylose (Merck 8689; store in desiccator) into 100 ml of buffer. Stock solution can be frozen in small aliquots at −20° C.; after thawing the tubes must be carefully mixed. Make the following dilutions from the stock solution in citrate buffer.

| Dilution | Xylose µmol/ml |
| --- | --- |
| 1:1 | 10.0 |
| 1:2 | 5.0 |
| 1:4 | 2.5 |
| 1:5 | 2.0 |

Do triplicate assays of each standard dilution in the same way as the enzyme blank. Pipette into test tubes 1.8 ml substrate, incubate 5 minutes at 50° C., acid 3.0 ml DNS and 200 µl standard dilution. Prepare the reagent blank by adding 200 µl citrate buffer instead of the standard dilution. Boil the tubes exactly 5 minutes, cool and measure the absorbance against the reagent blank at 540 nm. Construct a standard line for every series of assays.

EXAMPLE 9

An enzyme solution providing 90 FPU cellulase activity and 4300 IU xylanase activity per ml is used to treat 1000 kg of alfalfa hay having a moisture content 10%. 250 ml of the enzyme mixture is diluted in 50 l of water and sprayed onto the alfalfa hay just prior to baling. The final feed composition will have a moisture content of 15% and contain sufficient cellulase and xylanase to provide 25 FPU cellulase activity and 1194 IU xylanase activity per kga feed DM.

EXAMPLE 10

Two hundred ml of an enzyme solution containing 8000 IU xylanase and 200 FPU cellulase per ml in acetate buffer (100 mM sodium acetate; pH 5.0) is made up to 1.0 l with acetate buffer. The final solution contains 1600 IU xylanase/ml and 40 FPU cellulase/ml. The solution is sprayed onto whole barley grain at the rate of 1.0 l/tonne. The treated grain feed will contain sufficient cellulase and xylanase to provide 40 FPU cellulase/kg grain feed and 1600 IU xylanase/kg grain feed. The grain may be subsequently processed by rolling in a commercial roller mill.

EXAMPLE 11

Four parts of a powder having 10,000 IU xylanase activity/g is mixed with 1 part of a powder having 1000 FPU cellulase activity/g. The final mixture contains 8000 IU xylanase/g and 200 FPU cellulase/g. 400 g of the powder is dissolved in 5.0 l of a citrate buffer (50 mM sodium citrate; pH 4.5). The enzyme solution is sprayed onto alfalfa hay (8% moisture content) at a rate of 5.0 l/tonne. The resulting feed composition will contain sufficient cellulase and xylanase to provide 80 FPU cellulase/kg and 3200 IU xylanase/kg alfalfa forage. The resulting feed composition is then forced through dies in a commercial forage cubing mill to form cubes.

All publications mentioned in this specification are indicative of the level of skill of those skilled in the art to which this invention pertains. All publications are herein incorporated by reference to the same extent as if each individual publication was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

References

1. Feng, P., C. W. Hunt, W. E. Julien, K. Dickinson and T. Moen. 1992. Effect of enzyme additives on in situ and in vitro degradation of mature cool-season grass forage. J. Anim. Sci. 70 (Suppl. 1):309.
2. Feng, P., C. W. Hunt, W. E. Julian, S. C. Haeny and G. T. Pritchard. 1992. Effect of enzyme additives to cool-season grass forage on voluntary intake and digestive function in mature beef steers. J. Anim. Sci. 70 (Suppl. 1):310.
3. Chesson, A. 1994. Manipulation of fibre degradation—an old theme revisited. Pages 83–98 in T. P. Lyons and K. A. Jacques (Eds.). Biotechnology in the feed industry, Nottingham University Press. Loughborough, UK.
4. McAllister, T. A., H. D. Bae, L. J. Yanke, K. -J. Chang and J. K. Ha. 1994. A review of the microbial digestion of feed particles in the rumen. Asian J. Animal Sci. 7;303–316.
5. Gilbert, H. J., G. P. Hazlewood, J. I. Laurie, C. G. Orpin and G. P. Xue. 1992. Homologous catalytic domains in a rumen fungus xylanase: evidence for gene duplication and prokaryotic origin. Molec. Microbiology 6:2065.
6. Van Soest, P. J. 1982. Nutritional Ecology of the Ruminant. O&B Books. Corvallis, Oreg.
7. National Research Council. 1982. United States-Canadian Tables of Feed Composition, National Academy Press. Washington, D.C.
8. Nelson, C. J. and L. E. Moser. 1994. Plant factors affecting forage quality. Pages 115–154 in G. C. Fahey (ed.) Forage Quality and Utilization. American Society of Agronomy Inc., Madison, Wis.
9. Berger, L. L., G. C. Fahey, L. D. Bourquin and E. C. Titgemeyer. 1994. Modification of forage quality after harvest. In G. C. Fahey (ed.) Forage Quality and Utilization. American Society of Agronomy Inc., Madison, Wis.
10. Bailey, M. J. and K. Poutanen. 1989. Production of xylanase by strains of Aspergillus. Appl. Microbiol. Biotechnol. 30:5–10.
11. National Research Council. 1984. Nutrient Requirements of Beef Cattle (6th ed.) National Academy Press. Washington, D.C.
12. Goering, H. K. and P. J. Van Soest. 1970. Forage Fiber Analyses. Agriculture No. 379. Agriculture Research Service. United States Department of Agriculture.

We claim:

1. A feed composition comprising:
   a) a feed material selected from a legume forage, a grain feed, or a mixture thereof, the feed material having a moisture content of no greater than 15% (weight/weight) so that cellulase and xylanase in an aqueous solution are absorbed by and adhere to the feed material; and, b) a mixture of cellulase and xylanase absorbed into and adhering to the feed material, to form a stable feed composition for ruminants, the cellulase and xylanase provided in such amounts that the ratio of cellulase activity to xylanase activity is from about 2 to 5 filter paper units (FPU) cellulase activity per 100 international units (IU) xylanase activity.

2. The feed composition as set forth in claim 1, wherein the feed material is a legume forage.

3. The feed composition as set forth in claim 2 containing sufficient cellulase and xylanase to provide from about 16 to 120 FPU cellulase activity and from about 800 to 6000 IU xylanase activity per kg legume forage and wherein the ratio of cellulase activity to xylanase activity is from about 2 to 5 FPU cellulase activity per 100 IU xylanase activity.

4. The feed composition as set forth in claim 2 containing sufficient cellulase and xylanase to provide from about 18 to 72 FPU cellulase activity and from about 900 to 3600 IU xylanase activity per kg legume forage and wherein the ratio of cellulase activity to xylanase activity is from about 2 to 5 FPU cellulase activity per 100 IU xylanase activity.

5. The feed composition as set forth in claim 4, wherein the legume forage is alfalfa.

6. The feed composition as set forth in claim 1, wherein the feed material is a grain feed.

7. The feed composition as set forth in claim 6 containing sufficient cellulase and xylanase to provide from about 10 to 200 FPU cellulase activity and from about 500 to 10,000 IU xylanase activity per kg grain feed and wherein the ratio of cellulase activity to xylanase activity is from about 2 to 5 FPU cellulase activity per 100 IU xylanase activity.

8. The feed composition as set forth in claim 6 containing sufficient cellulase and xylanase to provide from about 40 to 160 FPU cellulase activity and from about 2000 to 8000 IU xylanase activity per kg grain feed and wherein the ratio of cellulase activity to xylanase activity is from about 2 to 5 FPU cellulase activity per 100 IU xylanase activity.

9. The feed composition as set forth in claim 8 wherein the grain feed is barley.

10. A method of producing a feed composition for comprising the steps of:

a) providing one or more aqueous solutions containing cellulase and xylanase enzymes separately or in admixture;

b) providing a feed material selected from a legume forage, a grain feed, or a mixture thereof, the feed material havig a moisture content no greater than 15% (weight/weight) so that when the aqueous solutions containing cellulase and xylanase are applied to the feed material, the cellulase and xylanase are absorbed by and adhere to the feed material;

c) applying the aqueous solutions containing cellulase and xylanase to the feed material to coat the feed material, the cellulase and xylanase provided in such amounts that the ratio of cellulase activity to xylanase activity is from about 2 to 5 filter paper units (FPU) cellulase activity per 100 international units (IU) xylanase activity;

d) incubating the feed material coated with the aqueous solutions until the xylanase and cellulase are absorbed into and adhere to the feed material, whereby a stable feed composition for ruminants is provided.

11. The method as set forth in claim 10, wherein in step (c), sufficiently small volumes of aqueous solutions are applied to the feed material that the moisture content of the feed material is not raised to above about 18%.

12. The method as set forth in claim 11, wherein in step (d), the feed material is incubated for at least about 3 hours.

13. The method as set forth in claim 12, wherein in step (d), the feed material is incubated for at least 8 hours.

14. The method as set forth in claim 12 wherein the feed material is a legume forage.

15. The method as set forth in claim 14 wherein sufficient cellulase and xylanase are applied to the feed material to provide from about 16 to 120 FPU cellulase activity and from about 800 to 6000 IU xylanase activity per kg legume forage and wherein the ratio of cellulase activity to xylanase activity is from about 2 to 5 FPU cellulase activity per 100 IU xylanase activity.

16. The method as set forth in claim 14 wherein sufficient cellulase and xylanase are applied to the feed material to provide from about 18 to 72 FPU cellulase activity and from about 900 to 3600 IU xylanase activity per kg legume forage and wherein the ratio of cellulase activity to xylanase activity is from about 2 to 5 FPU cellulase activity per 100 IU xylanase activity.

17. The method as set forth in claim 16 wherein the legume forage is alfalfa.

18. The method as set forth in claim 12 wherein the feed material is a grain feed.

19. The method as set forth in claim 18 wherein sufficient cellulase and xylanase are applied to the feed material to provide from about 10 to 200 FPU cellulase activity and from about 500 to 10,000 IU xylanase activity per kg grain feed and wherein the ratio of cellulase activity to xylanase activity is from about 2 to 5 FPU cellulase activity per 100 IU xylanase activity.

20. The method as set forth in claim 18 wherein sufficient cellulase and xylanase are applied to the feed material to provide from about 40 to 160 FPU cellulase activity and from about 2000 to 8000 IU xylanase activity per kg grain feed and wherein the ratio of cellulase activity to xylanase activity is from about 2 to 5 FPU cellulase activity per 100 IU xylanase activity.

21. The method as set forth in claim 20 wherein the grain feed is barley.

* * * * *

UNITED STATES PATENT AND TRADEMARK OFFICE
CERTIFICATE OF CORRECTION

PATENT NO. : 5,720,971

DATED : February 24, 1998

INVENTOR(S) : Beauchemin et al.

It is certified that error appears in the above-identified patent and that said Letters Patent is hereby corrected as shown below:

On the title page,

[73] "Assignee", please delete "Lacombe" and replace with --Lethbridge--.

[56] "References Cited", under "Foreign Patent Documents", please insert --.2-- after "88 105409".

"References Cited", under "Foreign Patent Documents", please insert --DD-- before "296 406 A5".

"References Cited", under "Foreign Patent Documents", line 6, at "296 407 A5", please delete --United Kingdom-- and replace with "Germany".

"References Cited", under "Foreign Patent Documents", line 10, at "92/01389", please insert --WO-- before "92/01389".

"References Cited", under "Foreign Patent Documents", line 11, at "92/10945", please insert --WO-- before "92/10945".

[57] "Abstract", line 9, please delete "cellulase and xylanase" and replace with --cellulases and xylanases--.

"Abstract", line 11, please delete "cellulase and xylanase" and replace with --cellulases and xylanases--.

"Abstract", line 17, please delete "cellulase and xylanase" and replace with --cellulases and xylanases--.

[56] "Other Publications", under "National Research Council", please delete "Tabels" and replace with --Tables--.

, under "Other Publications", under "Berge", please delete "Berge" and replace with --Berger--.

, under "Other Publications", under "Berge", please delete "Argonomy" and replace with --Agronomy--.

In column 4, line 12, please delete "ere" and replace with --are--.
In column 4, line 26, please delete "mixture" and replace with --mixtures--.
In column 4, line 63, please delete "absorbtion" and replace with --absorption--.
In column 4, line 67, please delete "absorbtion" and replace with --absorption--.

UNITED STATES PATENT AND TRADEMARK OFFICE
CERTIFICATE OF CORRECTION

PATENT NO. : 5,720,971                                 Page 2 of 4

DATED      : February 24, 1998

INVENTOR(S) : Beauchemin et al.

It is certified that error appears in the above-identified patent and that said Letters Patent is hereby corrected as shown below:

In column 5, line 10, please delete "Absorbtion" and replace with --Absorption--.
In column 5, line 24, please delete "osterases" and replace with --esterases--.
In column 5, line 29, please delete "Tho" and replace with --The--.
In column 6, line 47, please delete "foods" and replace with --feeds--.
In column 7, line 26, please delete "hemicelluse" and replace with --hemicellulose--.
In column 7, line 28, please delete "hemlcellulosic" and replace with --hemicellulosic--.
In column 7, line 57, please delete "kay" and replace with --hay--.
In column 9, line 25, please delete "feed" and replace with --fed--.
In column 9, line 30, please delete "cellulase" and replace with --cellulose--.
In column 9, line 31, please delete solubulizes" and replace with --solubilizes--.
In column 9, line 48, please delete "$\beta$-1-3" and replace with --$\beta$-1,3--.
In column 10, line 4, please delete "is" and replace with --are--.
In column 10, line 10, please delete "concentration" and replace with --concentrations--.
In column 12, line 13, please delete "flbrolytic" and replace with --fibrolytic--.
In column 12, line 15, please delete "or" and replace with --of--.
In column 12, line 17, please delete "(P=15)" and replace with --(P=0.15)--.
In column 14, line 48, please delete "pro-weighed" and replace with --pre-weighed--
In column 15, line 2, please delete "or" and replace with --of--.
In column 15, in Table 5, line 22, column 3, please delete "50.1" and replace with --50:1--.
In column 15, in Table 5, line 7, column 5, please delete "43.66" and replace with --43.56--.
In column 17, line 7, please delete "or" and replace with --of--.
In column 17, line 45, please delete "or" and replace with --of--.
In column 18, in Table 6, please delete the line spaces between "Alfalfa" and "silage".
In column 18, in Table 6, please delete the line spaces between "Digestibility" and "(%)".
In column 19, line 18, please insert a line space after "Equipment" and before the underline.
In column 19, line 27, please insert a space between "0.05" and "M" in both occurrences.

UNITED STATES PATENT AND TRADEMARK OFFICE
CERTIFICATE OF CORRECTION

PATENT NO. : 5,720,971  Page 3 of 4

DATED : February 24, 1998

INVENTOR(S) : Beauchemin et al.

It is certified that error appears in the above-identified patent and that said Letters Patent is hereby corrected as shown below:

In column 19, line 27, please insert --:-- after "(0.05 M, pH 4.8)".
In column 19, line 28, please delete "($C_8H_8O_7 \cdot H_2O$.)" and replace with --($C_6H_8O_7 \cdot H_2O$)
In column 19, line 29, please delete "($C_6H_5 Na_3O_7 \cdot 14.71$ g/l)" and replace with
  --($C_6H_5Na_3O_7 \cdot 2H_2O, 14.71$ g/l)--.
In column 19, line 30, please insert a space between "0.05" and "M" in both occurrences.
In column 19, line 33, please insert --:-- after "Substrate".
In column 19, line 37, please insert --:-- after "reagent".
In column 19, line 39, please delete "liters" and replace with --litres--.
In column 19, line 49, please insert --:-- after "Standard".
In column 19, line 57, please insert --of-- between "mg" and "glucose".
In column 19, line 62, please delete "Equillbrate" and replace with --Equilibrate--.
In column 19, line 65, please insert --,-- after "min.".
In column 19, line 65, please delete "incubation" and replace with --incubate--.
In column 19, line 65, please delete "add" and replace with --Add--.
In column 19, line 67, please delete "bland" and replace with --blank--.
In column 20, line 37, please delete "substraction" and replace with --subtraction--.
In column 20, line 38, please delete "or" and replace with --of--.
In column 21, line 9, please insert a space between "0.05" and "M" in both occurrences.
In column 21, line 9, please insert --:-- after "(0.05 M, pH 4.8)".
In column 21, line 11, please delete "$G_6H_6$" and replace with --$C_6H_5$--.
In column 21, line 22, please insert --:-- after "reagent".
In column 21, line 28, please delete "warned" and replace with --warmed--.
In column 21, line 38, please insert --5-- between "for" and "minutes."
In column 21, line 67, please delete "50 minutes" and replace with --5 minutes--.
In column 21, line 67, please delete "5°C." and replace with --50°C.--.
In column 22, line 14, please delete "Odinltrosalicylic" and replace with --dinitrosalicylic--.

UNITED STATES PATENT AND TRADEMARK OFFICE
CERTIFICATE OF CORRECTION

PATENT NO. : 5,720,971

DATED : February 24, 1998

INVENTOR(S) : Beauchemin et al.

It is certified that error appears in the above-identified patent and that said Letters Patent is hereby corrected as shown below:

In column 22, line 27, please delete "$\perp$" and replace with --$\pm$--.
In column 22, line 40, please delete "$C_8$" and replace with --$C_6$--.
In column 22, line 41, please delete "unit" and replace with --until--.
In column 23, line 29, please delete "acid" and replace with --add--.
In column 23, line 44, please delete "kga" and replace with --kg--.
In column 24, line 23, please delete "Julian" and replace with --Julien--.
In column 24, line 31, please delete "Chang" and replace with --Cheng--.
In column 25, line 40, please delete "for".
In column 25, line 47, please delete "havig" and replace with --having--.

Signed and Sealed this

Sixth Day of July, 1999

Attest:

Q. TODD DICKINSON

*Attesting Officer*    *Acting Commissioner of Patents and Trademarks*